US 8,221,725 B2

(12) United States Patent
Deckner et al.

(10) Patent No.: US 8,221,725 B2
(45) Date of Patent: *Jul. 17, 2012

(54) ORAL CARE COMPOSITIONS COMPRISING SPHERICAL FUSED SILICA

(75) Inventors: George Endel Deckner, Cincinnati, OH (US); Arif Ali Baig, Mason, OH (US); Iain Allan Hughes, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/624,703

(22) Filed: Nov. 24, 2009

(65) Prior Publication Data

US 2010/0135922 A1  Jun. 3, 2010

Related U.S. Application Data

(60) Provisional application No. 61/117,856, filed on Nov. 25, 2008.

(51) Int. Cl.
- *A61K 8/00* (2006.01)
- *A61K 8/18* (2006.01)
- *A61K 8/21* (2006.01)
- *A61K 8/30* (2006.01)
- *A61Q 11/00* (2006.01)

(52) U.S. Cl. ............................... 424/49; 424/52
(58) Field of Classification Search .................... 424/49, 424/52

See application file for complete search history.

(56) References Cited

U.S. PATENT DOCUMENTS

| | | | |
|---|---|---|---|
| 2,268,589 A | 1/1942 | Heany | |
| 3,538,230 A | 11/1970 | Pader et al. | |
| 3,696,191 A | 10/1972 | Weeks | |
| 3,862,307 A | 1/1975 | Di Giulio | |
| 3,978,205 A | 8/1976 | Newman et al. | |
| 3,991,008 A | 11/1976 | Temin et al. | |
| 4,165,368 A | 8/1979 | Gaffar | |
| 4,415,550 A | 11/1983 | Pakhomov et al. | |
| 4,442,240 A | 4/1984 | Suh | |
| 4,528,181 A | 7/1985 | Morton et al. | |
| 4,536,523 A | 8/1985 | Antonucci | |
| 4,575,456 A | 3/1986 | Hayes | |
| 4,685,946 A | 8/1987 | Derks et al. | |
| 4,774,267 A | 9/1988 | Weintraub | |
| 4,831,066 A | 5/1989 | Weintraub | |
| 4,923,520 A * | 5/1990 | Anzai et al. ................. 106/490 |
| 4,925,660 A | 5/1990 | Atsuta et al. | |
| 4,951,852 A | 8/1990 | Rancoulle | |

(Continued)

FOREIGN PATENT DOCUMENTS

JP  55-090555  7/1980

(Continued)

OTHER PUBLICATIONS

PCT International Search Report for PCT/US2009/065729 dated Aug. 6, 2010.

(Continued)

*Primary Examiner* — Benjamin Packard
(74) *Attorney, Agent, or Firm* — Armina E. Stricklin; David M. Weirich; Katherine Y. Carter

(57) ABSTRACT

An oral care composition comprising fused silica, wherein at least 25% of the fused silica particles are spherical.

10 Claims, 23 Drawing Sheets

| Silica Sample | Teco-Sil 44CSS | Teco-Sil 44C | Spheron N-2000R | 325F | RG 5 | RST 2500 DSO | Shinetsu | Teco-Sil 10 | Zeodent 109 | Zeodent 119 | Tixosil 73[1] | Tixosil 63[1] |
|---|---|---|---|---|---|---|---|---|---|---|---|---|
| Type | Fused | Fused | Fused | Fused | Fused | Fused | Fused | Fused | Ppt | Ppt | Ppt | Ppt |
| Particle shape | Angular | Angular | Spherical | Angular | Angular | Angular | Angular | Angular | | | | |
| Malvern PSD (microns) D[4,3] mean | 8.8 | 13.2 | 10.2 | 20.6 | 6.6 | 12.0 | 6.4 | 3.9 | 14.9 | 15.8 | | |
| D(0.1) | 1.5 | 1.6 | 1.8 | 2.2 | 1.6 | 1.6 | 1.4 | 1.4 | 2.8 | 3.3 | Median | Median |
| Median D(0.5) | 5.7 | 7.4 | 8.2 | 14.2 | 5.1 | 7.1 | 5.6 | 3.3 | 11.2 | 11.9 | D(0.5) | D(0.5) |
| D(0.9) | 20.6 | 32.8 | 21.0 | 48.9 | 13.8 | 29.2 | 12.2 | 7 | 32.7 | 34.0 | 9 | 9 |
| Span | 3.4 | 4.3 | 2.3 | 3.3 | 2.4 | 3.9 | 1.9 | 1.7 | 2.7 | 2.6 | | |
| Bulk density (g/mL) | 0.62 | 0.58 | 0.75 | 0.70 | 0.49 | 0.62 | - | - | 0.40 | 0.27 | 0.26 | 0.35 |
| Tapped density (g/mL) | 0.88 | 0.91 | 1.21 | 1.12 | 0.82 | 0.93 | - | - | 0.51 | 0.35 | 0.32 | 0.41 |
| Oil absorption (mL/100g) | 29.8 | 29.6 | 29.9 | 29.8 | 39.6 | 33.7 | - | - | 79.8 | 110.7 | 115 | 90 |
| Loss on drying (2 g @ 105°C for 2 hours) | 0.1% | 0.2% | 0.0% | 0.1% | 0.1% | 0.1% | - | - | 7.8% | 6.1% | 5.2% | 4.9% |
| Loss on ignition (1g @1000°C for 1 hour) | 2.2% | 1.0% | 0.8% | 0.5% | 0.6% | 1.1% | - | - | 4.8% | 5.1% | 8.5% | 8.3% |
| BET Surface Area - $N^2$ (m²/g) | 5.18 | 5.09 | 2.06 | 2.33 | 6.54 | 6.65 | 2.15 | 8.42 | 35.6 | 42.4 | 80 | 55 |
| Silanol density (int/g) | 574 | 520 | 47 | 154 | 556 | 797 | - | 1427 | 3919 | 3716 | - | - |

[1]Information from Rhodia precipitated silicas brochure

U.S. PATENT DOCUMENTS

| | | | |
|---|---|---|---|
| 5,004,488 A * | 4/1991 | Mehrotra et al. | 65/17.4 |
| 5,094,692 A | 3/1992 | Dumazeau et al. | |
| 5,172,963 A | 12/1992 | Brown | |
| 5,286,478 A | 2/1994 | Persello | |
| 5,484,581 A | 1/1996 | Esch et al. | |
| 5,538,714 A | 7/1996 | Pink et al. | |
| 5,612,020 A | 3/1997 | Persello | |
| 5,614,176 A | 3/1997 | Persello | |
| 5,614,177 A | 3/1997 | Persello | |
| 5,616,316 A | 4/1997 | Persello | |
| 5,624,652 A | 4/1997 | Aldcroft et al. | |
| 5,658,553 A | 8/1997 | Rice | |
| 5,744,114 A | 4/1998 | Persello | |
| 5,833,958 A | 11/1998 | Doel et al. | |
| 5,964,937 A | 10/1999 | Stanier | |
| 5,968,470 A | 10/1999 | Persello | |
| 5,989,524 A | 11/1999 | Dromard et al. | |
| 6,010,684 A | 1/2000 | Wiedemann | |
| 6,124,407 A | 9/2000 | Lee et al. | |
| 6,143,281 A | 11/2000 | Alexander et al. | |
| 6,280,707 B1 | 8/2001 | Peterson et al. | |
| 6,290,933 B1 * | 9/2001 | Durga et al. | 424/49 |
| 6,365,132 B1 | 4/2002 | Litkowski et al. | |
| 6,379,654 B1 | 4/2002 | Gebreselassie et al. | |
| 6,491,899 B1 | 12/2002 | Leinen et al. | |
| 6,506,366 B1 | 1/2003 | Leinen et al. | |
| 6,682,719 B2 | 1/2004 | Leinen et al. | |
| 6,685,919 B2 | 2/2004 | Leinen et al. | |
| 6,730,156 B1 | 5/2004 | Windisch et al. | |
| 6,795,409 B1 | 9/2004 | Youssefmir et al. | |
| 6,946,119 B2 | 9/2005 | Gallis et al. | |
| 7,255,852 B2 | 8/2007 | Gallis et al. | |
| 7,438,895 B2 | 10/2008 | Gallis | |
| 2001/0031245 A1 | 10/2001 | Scarlett-Smith | |
| 2002/0119231 A1 | 8/2002 | Kumamoto et al. | |
| 2002/0156152 A1 | 10/2002 | Zhang et al. | |
| 2002/0187108 A1 | 12/2002 | Rajaiah et al. | |
| 2003/0044359 A1 | 3/2003 | Wuelknitz | |
| 2003/0044442 A1 | 3/2003 | Stanier et al. | |
| 2004/0134230 A1 | 7/2004 | Kodas et al. | |
| 2004/0216486 A1 | 11/2004 | Schwertfeger et al. | |
| 2004/0241108 A1 | 12/2004 | Stanier et al. | |
| 2005/0129603 A1 * | 6/2005 | Szillat et al. | 423/335 |
| 2006/0088482 A1 | 4/2006 | Wulknitz | |
| 2006/0140878 A1 | 6/2006 | Cornelius et al. | |
| 2006/0222602 A1 | 10/2006 | Barth et al. | |
| 2007/0014740 A1 | 1/2007 | Miller et al. | |
| 2007/0154411 A1 | 7/2007 | Barth et al. | |
| 2007/0292458 A1 | 12/2007 | Stanier et al. | |
| 2008/0033117 A1 | 2/2008 | Ishii et al. | |
| 2008/0044796 A1 | 2/2008 | Hsu | |
| 2008/0154006 A1 | 6/2008 | Amagai et al. | |
| 2008/0187498 A1 | 8/2008 | Francis | |
| 2008/0274442 A1 | 11/2008 | Klee et al. | |
| 2008/0286214 A1 | 11/2008 | Brown et al. | |
| 2008/0286710 A1 | 11/2008 | Cinader et al. | |

FOREIGN PATENT DOCUMENTS

| | | |
|---|---|---|
| JP | 60-013708 | 1/1985 |
| JP | 60-178807 | 4/1985 |
| JP | 60-109516 | 6/1985 |
| JP | 61-072709 A | 4/1986 |
| JP | 2008-074772 | 4/2008 |
| WO | WO 93/23007 | 11/1993 |
| WO | WO 94/06868 | 3/1994 |
| WO | WO 96/10985 | 4/1996 |
| WO | WO 02/097021 | 12/2002 |
| WO | WO 2005/123023 | 12/2005 |

OTHER PUBLICATIONS

PCT International Search Report for PCT/US2009/065836 dated Jul. 6, 2010.

PCT International Search Report for PCT/US2009/065691 dated Jul. 6, 2010.

PCT International Search Report for PCT/US2009/065689 dated Jul. 6, 2010.

PCT International Search Report for PCT/US2009/065721 dated Aug. 6, 2010.

PCT International Search Report for PCT/US2009/065673 dated Jul. 6, 2010.

PCT International Search Report for PCT/US2009/065827 dated Aug. 6, 2010.

PCT International Search Report for PCT/US2009/065684 dated Jan. 29, 2010.

PCT International Search Report for PCT/US2009/065727 dated Jan. 20, 2010.

PCT International Search Report for PCT/US2009/065694 dated May 18, 2010.

U.S. Appl. No. 12/625,164, filed Nov. 24, 2009, Deckner et al.
U.S. Appl. No. 12/624,659, filed Nov. 24, 2009, Deckner et al.
U.S. Appl. No. 12/624,680, filed Nov. 24, 2009, Deckner et al.
U.S. Appl. No. 12/625,030, filed Nov. 24, 2009, Deckner et al.
U.S. Appl. No. 12/624,787, filed Nov. 24, 2009, Deckner et al.
U.S. Appl. No. 12/625,223, filed Nov. 24, 2009, Haught et al.
U.S. Appl. No. 12/624,585, filed Nov. 24, 2009, Deckner et al.
U.S. Appl. No. 12/624,883, filed Nov. 24, 2009, Baig et al.
U.S. Appl. No. 12/624,645, filed Nov. 24, 2009, Hughes et al.
U.S. Appl. No. 12/624,583, filed Nov. 24, 2009, Baig et al.
U.S. Appl. No. 12/624,617, filed Nov. 24, 2009, Baig et al.
U.S. Appl. No. 12/624,950, filed Nov. 24, 2009, Baig et al.
U.S. Appl. No. 12/624,812, filed Nov. 24, 2009, Baig et al.
U.S. Appl. No. 12/624,560, filed Nov. 24, 2009, Deckner et al.
U.S. Appl. No. 12/625,098, filed Nov. 24, 2009, Deckner et al.

DeRovira, Sr., D., Dictionary of Flavors, 2$^{nd}$ Ed., 2008, Wilely-Blackwell, p. 669.

Gent, Janneane F. et al., Taste Confusions following Chlorhexidine Treatment, Chemical Senses, 2002, 27, pp. 73-80.

Jacobs, Frederic Burnham, "Abrasives & Abrasive Wheels, Their Nature, Manufacture . . ", House & Home, 1919, p. 36.

Lai, K., Liquid Detergents, 2006, Second Edition, Taylor & Francis Group, pp. 564.

Otera et al., Chapter 8, Industrial Uses/Flavoring Agents and Fragrances, Esterification, 2010, Wiley-VCH, pp. 310, 312-314, 319 and 320.

* cited by examiner

| Silica Sample | Teco-Sil 44CSS | Teco-Sil 44C | Spheron N-2000R | 325F | RG 5 | RST 2500 DSO | Shinetsu | Teco-Sil 10 | Zeodent 109 | Zeodent 119 | Tixosil 73[1] | Tixosil 63[1] |
|---|---|---|---|---|---|---|---|---|---|---|---|---|
| Type | Fused | Fused | Fused | Fused | Fused | Fused | Fused | Fused | Ppt | Ppt | Ppt | Ppt |
| Particle shape | Angular | Angular | Spherical | Angular | Angular | Angular | Angular | Angular | | | | |
| Malvern PSD (microns) D[4,3] mean | 8.8 | 13.2 | 10.2 | 20.6 | 6.6 | 12.0 | 6.4 | 3.9 | 14.9 | 15.8 | | |
| D(0.1) | 1.5 | 1.6 | 1.8 | 2.2 | 1.6 | 1.6 | 1.4 | 1.4 | 2.8 | 3.3 | Median | Median |
| Median D(0.5) | 5.7 | 7.4 | 8.2 | 14.2 | 5.1 | 7.1 | 5.6 | 3.3 | 11.2 | 11.9 | D(0.5) | D(0.5) |
| D(0.9) | 20.6 | 32.8 | 21.0 | 48.9 | 13.8 | 29.2 | 12.2 | 7 | 32.7 | 34.0 | 9 | 9 |
| Span | 3.4 | 4.3 | 2.3 | 3.3 | 2.4 | 3.9 | 1.9 | 1.7 | 2.7 | 2.6 | | |
| Bulk density (g/mL) | 0.62 | 0.58 | 0.75 | 0.70 | 0.49 | 0.62 | - | - | 0.40 | 0.27 | 0.26 | 0.35 |
| Tapped density (g/mL) | 0.88 | 0.91 | 1.21 | 1.12 | 0.82 | 0.93 | - | - | 0.51 | 0.35 | 0.32 | 0.41 |
| Oil absorption (mL/100g) | 29.8 | 29.6 | 29.9 | 29.8 | 39.6 | 33.7 | - | - | 79.8 | 110.7 | 115 | 90 |
| Loss on drying (2 g @ 105°C for 2 hours) | 0.1% | 0.2% | 0.0% | 0.1% | 0.1% | 0.1% | - | - | 7.8% | 6.1% | 5.2% | 4.9% |
| Loss on ignition (1g @1000°C for 1 hour) | 2.2% | 1.0% | 0.8% | 0.5% | 0.6% | 1.1% | - | - | 4.8% | 5.1% | 8.5% | 8.3% |
| BET Surface Area - N² (m²/g) | 5.18 | 5.09 | 2.06 | 2.33 | 6.54 | 6.65 | 2.15 | 8.42 | 35.6 | 42.4 | 80 | 55 |
| Silanol density (int/g) | 574 | 520 | 47 | 154 | 556 | 797 | - | 1427 | 3919 | 3716 | - | - |

[1] Information from Rhodia precipitated silicas brochure

Fig. 1

| Silica Sample | Teco-Sil 44CSS | Spheron N-2000R | 325F | RG 5 | RST 2500 DSO | Zeodent 109 | Zeodent 119 |
|---|---|---|---|---|---|---|---|
| Sn compatibility (%) | 93.5 | 100 | 100 | 93.9 | 93.1 | 53.1 | 43.7 |
| F compatibility (%) | 98.4 | 100 | 100 | 100 | 100 | 84.9 | 77.2 |

Fig. 2

| Ingredient | Formula A | Formula B | Formula C | Formula D | Formula E |
|---|---|---|---|---|---|
| Sorbitol Solution (70% soln) | 70.5 | 65.5 | 65.5 | 65.5 | 65.5 |
| Tecosil 44CSS | 10 | 15 | - | - | - |
| Silica Z119 | - | - | 20 | - | - |
| Silica Z109 | - | - | - | 10 | 15 |
| Sodium Lauryl Sulfate 28% Solution | 4 | 4 | 4 | 4 | 4 |
| Tribasic Sodium Phosphate Dodecahydrate | 1.1 | 1.1 | 1.1 | 1.1 | 1.1 |
| Flavor | 0.8 | 0.8 | 0.8 | 0.8 | 0.8 |
| Carboxymethylcellulose Sodium | 0.75 | 0.75 | 0.75 | 0.75 | 0.75 |
| Titanium Dioxide | 0.53 | 0.53 | 0.53 | 0.53 | 0.53 |
| Sodium Phosphate, Monobasic, Monohydrate, USP | 0.42 | 0.42 | 0.42 | 0.42 | 0.42 |
| Carbomer 956 | 0.3 | 0.3 | 0.3 | 0.3 | 0.3 |
| Sodium Fluoride | 0.24 | 0.24 | 0.24 | 0.24 | 0.24 |
| Saccharin Sodium | 0.13 | 0.13 | 0.13 | 0.13 | 0.13 |
| FD&C Blue #1 | 0.05 | 0.05 | 0.05 | 0.05 | 0.05 |
| Water | QS | QS | QS | QS | QS |

Fig. 3A

| | Formula A | Formula B | Formula C | Formula D | Formula E |
|---|---|---|---|---|---|
| Silica Type | Tecosil 44CSS | Tecosil 44CSS | Zeodent 119 | Zeodent 109 | Zeodent 109 |
| Amount of silica (%) | 10% | 15% | 20% | 10% | 15% |
| RDA | 169.75 | 218.03 | 127.61 | 139.56 | 75.36 |
| PCR | 128.2 | 128 | 113.4 | 113.8 | - |

Fig. 3B

| Ingredient | Formula A | Formula B | Formula C | Formula D | Formula E | Formula F | Formula G | Formula H |
|---|---|---|---|---|---|---|---|---|
| Sorbitol Solution (70% soln) | 39.85 | 39.85 | 39.85 | 39.85 | 39.85 | 39.85 | 39.85 | 39.85 |
| Tecosil 44CSS | 15.00 | - | - | - | - | - | - | 7.5 |
| Tecosil 44C | - | 15.00 | - | - | - | - | - | - |
| Spheron N2000R | - | - | 15.00 | - | - | - | - | - |
| 325F | - | - | - | 15.00 | - | - | - | - |
| RG5 | - | - | - | - | 15.00 | - | - | - |
| RST 2500DSO | - | - | - | - | - | 15.00 | - | - |
| Silica Z119 | - | - | - | - | - | - | 15.00 | - |
| Silica Z109 | - | - | - | - | - | - | - | 7.5 |
| Sodium Lauryl Sulfate 28% Soln. | 5.00 | 5.00 | 5.00 | 5.00 | 5.00 | 5.00 | 5.00 | 5.00 |
| Stannous Chloride Dihydrate | 1.16 | 1.16 | 1.16 | 1.16 | 1.16 | 1.16 | 1.16 | 1.16 |
| Sodium Gluconate, USP | 1.06 | 1.06 | 1.06 | 1.06 | 1.06 | 1.06 | 1.06 | 1.06 |
| Phytic Acid 50% Solution | 0.80 | 0.80 | 0.80 | 0.80 | 0.80 | 0.80 | 0.80 | 0.80 |
| Zinc Citrate Dihydrate | 0.53 | 0.53 | 0.53 | 0.53 | 0.53 | 0.53 | 0.53 | 0.53 |
| Flavor | 0.80 | 0.80 | 0.80 | 0.80 | 0.80 | 0.80 | 0.80 | 0.80 |
| Carboxymethylcellulose Sodium | 1.30 | 1.30 | 1.30 | 1.30 | 1.30 | 1.30 | 1.30 | 1.30 |
| Titanium Dioxide | 0.53 | 0.53 | 0.53 | 0.53 | 0.53 | 0.53 | 0.53 | 0.53 |
| Carrageenan | 0.70 | 0.70 | 0.70 | 0.70 | 0.70 | 0.70 | 0.70 | 0.70 |
| Sodium Hydroxide | 0.58 | 0.58 | 0.58 | 0.58 | 0.58 | 0.58 | 0.58 | 0.58 |
| Sodium Fluoride | 0.24 | 0.24 | 0.24 | 0.24 | 0.24 | 0.24 | 0.24 | 0.24 |
| Saccharin Sodium | 0.50 | 0.50 | 0.50 | 0.50 | 0.50 | 0.50 | 0.50 | 0.50 |
| Hydroxyethyl cellulose | 0.50 | 0.50 | 0.50 | 0.50 | 0.50 | 0.50 | 0.50 | 0.50 |
| Water | QS | QS | QS | QS | QS | QS | QS | QS |

Fig. 4A

|  | Formula A | Formula B | Formula C | Formula D | Formula E | Formula F | Formula G | Formula H |
|---|---|---|---|---|---|---|---|---|
| Silica Sample | Teco-Sil 44CSS | Teco-Sil 44C | Spheron N-2000R | 325F | RG 5 | RST 2500 DSO | Z-109 | Teco-Sil 44CSS and Z-109 |
| Amount of silica | 15% | 15% | 15% | 15% | 15% | 15% | 15% | 15% |
| PCR | 148.5 | 143 | 132.9 | 126.8 | 133.4 | 129.3 | 115.8 | 145.88 |
| RDA | 176.7 | 169.4 | 142.6 | 158.6 | 155.4 | 141.4 | 127.3 | 125.1 |

Fig. 4B

| RDA Data | | | | |
|---|---|---|---|---|
| Silica Load | Z119 | Z109 | TS10 | TS44CSS |
| 5% | 43.28 | 111.29 | 136.56 | 153.58 |
| 10% | 57.17 | 134.63 | 152.01 | 200.94 |
| 15% | 74.8 | 176.53 | 183.31 | 229.62 |
| PCR data | | | | |
| Silica Load | Z119 | Z109 | TS10 | TS44CSS |
| 5% | 73.1 | 77.1 | 87.7 | 80.9 |
| 10% | 85.4 | 89.2 | 106.6 | 113.5 |
| 15% | 79.3 | 103.5 | 93.9 | 124.4 |

Fig. 5

| Ingredient | Formula A | Formula B |
|---|---|---|
| SnF2, USP | 0.45 | 0.45 |
| Zinc citrate | 0.50 | 0.50 |
| Zinc Lactate | - | - |
| Sorbitol(LRS) USP | 45.00 | 45.00 |
| Fused Silica (TecoSil 44CSS) | - | 15.00 |
| Silica Z119 | 2.50 | 0.00 |
| Silica Z109 | 12.50 | 0.00 |
| Hydroxyethyl cellulose (HEC Natrasol 250M) | 0.50 | 0.50 |
| CMC 7M8SF | 1.30 | 1.30 |
| Carrageenan mixture | 0.70 | 0.70 |
| Sodium lauryl sulfate (48397-002) | 4.00 | 4.00 |
| Saccharin Sodium | 0.50 | 0.50 |
| Sodium Gluconate | 1.00 | 1.00 |
| Flavor | 1.00 | 1.00 |
| Water, USP | QS | QS |

Fig. 7A

| Sample | pH | Temp | Time | % Compatibility | | |
|---|---|---|---|---|---|---|
| | | | | Stannous | Fluoride | Zinc |
| Formula A | 4.62 | 25C | 2 weeks | 59.12 | 86.00 | 81.69 |
| | | | 1 month | 49.04 | 86.27 | 70.84 |
| | | | 2 month | 54.70 | 85.09 | 78.80 |
| Formula A | | 40 C | 2 weeks | 52.89 | 83.82 | 81.69 |
| | | | 1 month | 46.21 | 80.09 | 72.77 |
| | | | 2 month | 52.21 | 79.55 | 78.80 |
| Formula B | 4.41 | 25C | 2 weeks | 100.11 | 96.91 | 95.90 |
| | | | 1 month | 85.50 | 95.55 | 82.65 |
| | | | 2 month | 92.64 | 94.45 | 92.29 |
| Formula B | | 40 C | 2 weeks | 98.19 | 94.27 | 95.66 |
| | | | 1 month | 93.43 | 93.09 | 92.53 |
| | | | 2 month | 91.39 | 93.36 | 93.73 |

Fig. 7B

| Z119 load (%) | Z119 Load (g) | % Free Stannous |
|---|---|---|
| 2 | 1.00 | 86.87 |
| 5 | 2.50 | 83.22 |
| 10 | 5.00 | 73.52 |
| 16 | 8.00 | 61.23 |
| 25 | 12.50 | 32.13 |

Stannous loss per gram of silica Z119 = 0.0081g/g of Z119 (80 ppm / 1 % Z119 Load)
Stannous loss per gram of Fused silica = 0.001g/g of Tecosil 44CSS (10 ppm / 1 % Tecosil 44CSS Load)

Fig. 8

| Sample | Silica Type | Gel Base (g) Whitening Booster gel (Arm and Hammer) | Silica (g) | Glycerin (g) | Total (g) |
|---|---|---|---|---|---|
| Control (no abrasive) | Control | 18.00 | 0.00 | 2.00 | 20.00 |
| Z109 | Z109 | 18.00 | 2.00 | 0.00 | 20.00 |
| Z119 | Z119 | 18.00 | 2.00 | 0.00 | 20.00 |
| TS44CSS | Teco-Sil 44CSS | 18.00 | 2.00 | 0.00 | 20.00 |
| SPP1500 | Spheron P1500 | 18.00 | 2.00 | 0.00 | 20.00 |
| SPN2000 | Spheron N2000R | 18.00 | 2.00 | 0.00 | 20.00 |
| SS130NP | Sun-Sil 130NP | 18.00 | 2.00 | 0.00 | 20.00 |
| 325F | 325F | 18.00 | 2.00 | 0.00 | 20.00 |
| RG5 | RG5 | 18.00 | 2.00 | 0.00 | 20.00 |
| RST2500 | RST 2500 DSO | 18.00 | 2.00 | 0.00 | 20.00 |

Fig. 9A

| Sample | H2O2 (% remaining) | | | % Compatibility (13 days) |
|---|---|---|---|---|
| | Initial | 6 Days | 13 Days | |
| Control (no abrasive) | 2.12 | 1.93 | 2.16 | 100.0 |
| Z109 | 2.09 | 1.23 | 0.51 | 23.6 |
| Z119 | 2.29 | 1.37 | 0.18 | 8.3 |
| TS44CSS | 1.92 | 1.92 | 1.84 | 85.1 |
| SPP1500 | 2.06 | 1.92 | 1.83 | 84.9 |
| SPN2000 | 1.89 | 1.88 | 1.82 | 84.4 |
| SS130NP | 1.96 | 1.86 | 1.85 | 85.5 |
| 325F | 1.88 | 1.89 | 1.87 | 86.7 |
| RG5 | 1.89 | 1.87 | 2.16 | 100.0 |
| RST2500 | 1.92 | 1.94 | 1.89 | 87.5 |

| Ingredient | Peroxide + SN + Carageenan Formula A | Peroxide + MFP + Chelant Formula B | Peroxide + Sn + CMC Formula C | Peroxide + Sn + Gel Network Formula D | Peroxide + Chelant + Gel Network Formula E | Tecosil 44CSS + NaF Formula F |
|---|---|---|---|---|---|---|
| Glycerin | 10.00 | 30.00 | 30.00 | 10.00 | 30.00 | |
| Sorbitol | 20.00 | - | - | 20.00 | - | 39.85 |
| Sodium Gluconate | 1.00 | - | 1.00 | 1.00 | - | |
| SnF2, USP | 0.45 | - | 0.45 | 0.45 | - | |
| Sodium fluoride | | | | | | 0.24 |
| Sodium monofluorophosphate | | 1.10 | - | - | 1.10 | |
| Hydrogen Peroxide (35% soln) | 4.30 | 4.30 | 8.60 | 8.60 | 8.60 | |
| Stannous chloride | | 0.10 | - | - | 0.10 | |
| Pemulen TR2 | 0.50 | - | - | - | - | |
| Carrageenan | 1.00 | 1.00 | - | - | 1.00 | |
| Sodium lauryl sulfate (powder) | 1.00 | 2.00 | 1.00 | 1.00 | 2.00 | 4.00 |
| Cocoamidopropyl Betaine (30% Soln) | 0.5 | 0.50 | - | 0.50 | 0.50 | |
| Sodium hexametaphosphate | - | 10.00 | - | - | 10.00 | |
| Sodium tripolyphopshate | - | - | - | - | - | |
| Carboxymethyl cellulose | - | - | 4.00 | - | - | 1.3 |
| Tribasic Sodium Phosphate Dodecahydrate | | | | | | 1.1 |
| Sodium Phosphate Monobasic Monohydrate | | | | | | 0.42 |
| Titanium dioxide | - | - | - | 3.00 | - | 0.53 |
| Carbomer 956 | - | - | - | 3.00 | - | |
| Carrageenan | - | 2.00 | - | - | - | |
| Hydroxyethyl cellulose | | | | | | 0.7 |
| Tecosil 44CSS | 10.00 | 10.00 | 10.00 | 10.00 | 10.00 | 10.00 |
| Saccharin Sodium | 0.50 | 0.50 | 0.50 | 0.50 | 0.50 | 0.50 |
| Cetyl Alcohol | - | - | - | 3.00 | 3.00 | |
| Strearyl Alcohol | - | - | - | 3.00 | 3.00 | |
| Flavor | 1.20 | 1.20 | 1.20 | 1.20 | 1.20 | 0.80 |
| Water | QS | QS | QS | QS | QS | QS |

| | ΔL 50 stroke | ΔL 100 stroke | ΔL 200 stroke | ΔL 400 stroke |
|---|---|---|---|---|
| Crest Cavity Prevention Toothpaste | 2.94 | 4.07 | 5.61 | 8.10 |
| Formula F | 4.11 | 5.87 | 8.95 | 13.43 |
| Formula C | 6.05 | 9.14 | 14.57 | 24.09 |
| Formula D | 9.49 | 16.06 | 24.55 | 35.80 |

Fig. 10B

| Ingredient | Formula A | Formula B | Formula C | Formula D | Formula E | Formula F |
|---|---|---|---|---|---|---|
| Sorbitol Solution (70% soln) | 39.85 | 39.85 | 39.85 | 39.85 | 39.85 | 39.85 |
| Tecosil 44CSS | - | 15.00 | - | - | - | - |
| Spheron N2000R | - | - | 15.00 | - | - | - |
| RG5 | - | - | - | 15.00 | - | - |
| Spheron P-1500 | - | - | - | - | 15.00 | - |
| Amatech (Shinetsu) | - | - | - | - | - | 15.00 |
| Silica Z109 | 15.00 | - | - | - | - | - |
| Sodium Lauryl Sulfate 28% Soln. | 5.00 | 5.00 | 5.00 | 5.00 | 5.00 | 5.00 |
| Tribasic Sodium Phosphate Dodecahydrate | 1.10 | 1.10 | 1.10 | 1.10 | 1.10 | 1.10 |
| Sodium Phosphate Monobasic Monohydrate | 0.42 | 0.42 | 0.42 | 0.42 | 0.42 | 0.42 |
| Flavor | 0.80 | 0.80 | 0.80 | 0.80 | 0.80 | 0.80 |
| Carboxymethylcellulose Sodium | 1.30 | 1.30 | 1.30 | 1.30 | 1.30 | 1.30 |
| Titanium Dioxide | 0.53 | 0.53 | 0.53 | 0.53 | 0.53 | 0.53 |
| Carrageenan | 0.70 | 0.70 | 0.70 | 0.70 | 0.70 | 0.70 |
| Sodium Fluoride | 0.24 | 0.24 | 0.24 | 0.24 | 0.24 | 0.24 |
| Saccharin Sodium | 0.50 | 0.50 | 0.50 | 0.50 | 0.50 | 0.50 |
| Hydroxyethyl cellulose | 0.50 | 0.50 | 0.50 | 0.50 | 0.50 | 0.50 |
| Water | QS | QS | QS | QS | QS | QS |

Fig. 11A

|  | Formula A | Formula B | Formula C | Formula D | Formula E | Formula F |
|---|---|---|---|---|---|---|
|  | Zeodent 109 | Tecosil 44CSS | Spheron 2000 | RG5 | Spheron P1500 | Shinetsu |
| During use | | | | | | |
| Flavor Intensity | 4.11 | 4.28 | 4.22 | 4.22 | 4.11 | 4.67 |
| Refreshment/Cooling | 3.61 | 4.39 | 4.22 | 4.72 | 4.33 | 4.33 |
| Immediately after use | | | | | | |
| Flavor Intensity | 3.61 | 4.22 | 4.39 | 4.11 | 4.22 | 4.56 |
| Clean Mouth feel | 3.94 | 4.56 | 4.5 | 4.61 | 4.44 | 4.44 |
| Slick tooth feel | 3.44 | 3.83 | 4.22 | 4.5 | 3.83 | 3.89 |
| Tongue and Gum feel | 1.83 | 2.67 | 2.11 | 2.56 | 1.78 | 1.89 |
| Refreshment/Cooling | 3.39 | 4.33 | 4.44 | 4.33 | 4.06 | 4.67 |
| 15 minutes after use | | | | | | |
| Flavor Intensity | 2.22 | 2.89 | 2.78 | 2.33 | 2.61 | 2.67 |
| Clean Mouth feel | 3.11 | 3.5 | 3.61 | 3.94 | 3.5 | 3.78 |
| Slick tooth feel | 2.72 | 3.17 | 3.39 | 4 | 3.11 | 3.56 |
| Refreshment/Cooling | 1 | 1.39 | 1.83 | 1.11 | 1.06 | 2.11 |

| Ingredient | Gel Network Formula A | FS+Z119 Formula B | FS+CaCO3 Formula C | SLS Free MFP Formula D | SLS Free NaF Formula E | Prophy Paste Formula F | Non-Daily Paste Formula G |
|---|---|---|---|---|---|---|---|
| Sodium Gluconate | 1.064 | 1.064 | - | - | - | - | - |
| Stannous fluoride | 0.454 | 0.454 | - | - | - | - | - |
| Sodium fluoride | | | - | - | 0.243 | 0.243 | - |
| Sodium monofluorophosphate | | | 1.10 | 1.10 | - | - | - |
| Zinc Lactate | 0.670 | 0.670 | - | - | - | - | - |
| Glycerin | - | - | - | - | - | 40.000 | 40.000 |
| Polyethylene glycol 300 | | | | | | | 3.000 |
| Sorbitol(LRS) USP | 39.612 | 39.612 | 24.000 | 24.000 | 42.500 | - | - |
| Sodium lauryl sulfate solution (28%) | 5.000 | 5.000 | 4.000 | - | - | - | 5.000 |
| Tecosil 44CSS | 10.000 | 5.000 | 5.000 | 5.000 | 10.000 | 15.000 | 15.000 |
| Zeodent 119 | - | 10.000 | - | - | - | - | - |
| Sodium hexametaphosphate | - | - | - | - | - | - | 14.000 |
| Natural CaCO3-600M | - | - | 42.00 | 42.00 | - | - | - |
| Sodium phosphate (mono basic) | - | - | 0.10 | 0.10 | 0.420 | 0.420 | 0.420 |
| Sodium phosphate (Tri basic) | - | - | 0.40 | 0.40 | 1.100 | 1.100 | 1.100 |
| Zeodent 165 | - | - | 2.00 | 2.00 | - | 2.000 | 2.000 |
| Cocoamidopropyl Betaine (30% Soln) | - | - | 0.000 | 6.000 | 6.000 | - | - |
| Cetyl Alcohol | 3.000 | 0.000 | 0.000 | 0.000 | - | - | - |
| Stearyl Alcohol | 3.000 | 0.000 | 0.000 | 0.000 | - | - | - |

Fig. 12A

| | | | | | | |
|---|---|---|---|---|---|---|
| Hydroxyethyl cellulose (HEC Natrasol 250M) | - | 0.500 | - | - | - | 0.500 | - |
| CMC 7M8SF | - | 1.300 | 1.300 | 1.300 | 1.300 | 1.300 | 1.000 |
| Xanthan Gum | - | - | - | - | - | - | 0.300 |
| Poloxamer 407 | - | - | - | - | - | - | 0.500 |
| Carrageenan mixture | - | 0.700 | - | - | 0.700 | - | - |
| Titanium dioxide | 0.500 | - | - | - | - | - | 0.500 |
| Saccharin Sodium | - | 0.500 | 0.250 | 0.250 | 0.500 | 0.500 | 0.500 |
| Flavor | 1.000 | 1.000 | 1.000 | 1.000 | 1.000 | 1.000 | 1.000 |
| Water | QS | QS | QS | QS | QS | QS | QS |

Fig. 12B

| Ingredient | A | B | C | D | E | F |
|---|---|---|---|---|---|---|
| Sodium Fluoride | 0.24 | 0.24 | 0.24 | 0.24 | 0.24 | 0.24 |
| Sorbitol | 60.2 | 60.2 | 40.0 | 40.0 | 37.5 | 37.5 |
| Glycerin | - | - | - | - | - | - |
| Silica (Zeodent 119) | 20 | - | - | - | - | - |
| Silica (Zeodent 109) | - | 20 | - | - | - | - |
| Fused Silica (Teco-Sil 44CSS) | - | - | - | 15.0 | - | 15.0 |
| Fused Silica (Teco-Sil 10 | - | - | 15.0 | - | 15.0 | - |
| Flavor | 0.9 | 0.9 | 1.0 | 1.0 | 1.0 | 1.0 |
| Carbomer | 0.30 | 0.30 | - | - | - | - |
| Hydroxyethyl cellulose | - | - | 0.5 | 0.5 | - | - |
| Carrageenan | - | - | 0.7 | 0.7 | - | - |
| Xanthan Gum | 0.48 | 0.48 | - | - | - | - |
| Carboxymethyl cellulose | - | - | 1.3 | 1.3 | - | - |
| Trisodium phosphate | 1.45 | 1.45 | 0.41 | 0.41 | 0.41 | 0.41 |
| Monosodium phosphate | 0.59 | 0.59 | 0.42 | 0.42 | 0.42 | 0.42 |
| Cetyl Alcohol | - | - | - | - | 2.0 | 2.0 |
| Strearyl Alcohol | - | - | - | - | 2.0 | 2.0 |
| Titanium Dioxide | 0.52 | 0.52 | 0.52 | 0.52 | 0.52 | 0.52 |
| Saccharin Sodium | 0.13 | 0.13 | 0.50 | 0.50 | 0.50 | 0.50 |
| Sodium Lauryl Sulfate (28% soln) | 4.0 | 4.0 | 5.0 | 5.0 | 4.0 | 4.0 |
| Water | QS | QS | QS | QS | QS | QS |
| | 100.00 | 100.00 | 100.00 | 100.00 | 100.00 | 100.00 |

Fig. 13A

| Treatment | Formula | RDA | PCR |
|---|---|---|---|
| 20% Z119 in NaF base | A | 129.01 | 82.22 |
| 20% Z109 in NaF base | B | 191.93 | 88.53 |
| 15% Tecosil 10 in NaF base | C | 144.11 | 92.5 |
| 15% TS 44CSS in NaF base | D | 214.42 | 95.44 |
| 15% Tecosil 10 in NaF GN base | E | 236.37 | 127.56 |
| 15% TS 44CSS in NaF GN base | F | 277.22 | 121.04 |

Fig. 13B

| Ingredient | A | B | C | D | E | F |
|---|---|---|---|---|---|---|
| Sodium Fluoride | 0.24 | 0.24 | 0.24 | 0.24 | 0.24 | 0.24 |
| Stannous Chloride | 1.16 | 1.16 | 1.16 | 1.16 | 1.16 | 1.16 |
| Sodium gluconate | 1.06 | 1.06 | 1.06 | 1.06 | 1.06 | 1.06 |
| Zinc Citrate | 0.53 | 0.53 | 0.53 | 0.53 | 0.53 | 0.53 |
| Phytic acid | 0.80 | 0.80 | 0.80 | 0.80 | 0.80 | 0.80 |
| Sorbitol | 39.85 | 39.85 | 34.85 | 34.85 | 38.35 | 38.35 |
| Silica (Zeodent 119) | 20 | - | - | - | - | - |
| Silica (Zeodent 109) | - | 20 | - | - | - | - |
| Fused Silica (Teco-Sil 44CSS) | - | - | - | - | - | - |
| Fused Silica (Teco-Sil 10) | - | - | 15 | 15 | 15 | 15 |
| Flavor | 1.0 | 1.0 | 1.0 | 1.0 | 1.0 | 1.0 |
| Carboxymethylcellulose Sodium | 1.30 | 1.30 | 1.30 | 1.30 | - | - |
| Carrageenan | 0.70 | 0.70 | 0.70 | 0.70 | - | - |
| Hydroxyethyl cellulose | 0.50 | 0.50 | 0.50 | 0.50 | - | - |
| Cetyl Alcohol | - | - | - | - | 2.0 | 2.0 |
| Strearyl Alcohol | - | - | - | - | 2.0 | 2.0 |
| Titanium Dioxide | 0.52 | 0.52 | 0.52 | 0.52 | 0.52 | 0.52 |
| Saccharin Sodium | 0.50 | 0.50 | 0.50 | 0.50 | 0.50 | 0.50 |
| Sodium Lauryl Sulfate | 5.0 | 5.0 | 5.0 | 5.0 | 5.0 | 5.0 |
| Water | QS | QS | QS | QS | QS | QS |
| | 100.00 | 100.00 | 100.00 | 100.00 | 100.00 | 100.00 |

Fig. 13C

| Treatment | Formula | RDA |
|---|---|---|
| 20% 119 in Sn base | A | 86.26 |
| 20% 109 in Sn base | B | 181.28 |
| 15% Tecosil 10 in Sn base | C | 165.33 |
| 15% TS 44CSS in Sn base | D | 195.92 |
| 15% Tecosil 10 in Sn GN base | E | 188.87 |
| 15% TS 44CSS in Sn GN base | F | 219.43 |

Fig. 13D

ORAL CARE COMPOSITIONS COMPRISING SPHERICAL FUSED SILICA

CROSS REFERENCE TO RELATED APPLICATION

This application claims the benefit of U.S. Provisional Application No. 61/117,856, filed Nov. 25, 2008, the entire substance of which is incorporated herein by reference.

FIELD OF THE INVENTION

The present invention relates to oral care compositions comprising fused silica, wherein at least 25% of the fused silica particles are spherical.

BACKGROUND OF THE INVENTION

An effective oral composition can maintain and preserve tooth appearance by removing dental stains and polishing the teeth. It may clean and remove external debris as well, which can aid the prevention of tooth decay and promote gingival health.

Abrasives in oral compositions aid in the removal of the tightly adherent pellicle film to which dental stains affix. Pellicle film usually comprises a thin acellular, glycoprotein-mucoprotein coating, which adheres to the enamel within minutes after teeth are cleaned. The presence of various food pigments lodged within the film accounts for most instances of teeth discoloration. An abrasive may remove the pellicle film with minimal abrasive damage to oral tissue, such as the dentin and enamel.

In addition to cleaning, it may be desirable for abrasive systems to provide polishing of tooth surfaces, as polished surfaces may be more resistant to ectopic deposition of undesirable components. Tooth appearance may be improved by imparting a polished character to the teeth, because the surface roughness, that is, its polish, affects light reflectance and scattering, which integrally relate to the teeth's visual appearance. The surface roughness also affects tooth feel. For example, polished teeth have a clean, smooth, and slick feel.

Numerous dentifrice compositions use precipitated silicas as abrasives. Precipitated silicas are noted and described in U.S. Pat. No. 4,340,583, Jul. 20, 1982, to Wason, EP Patent 535,943A1, Apr. 7, 1993, to McKeown et al., PCT Application WO 92/02454, Feb. 20, 1992 to McKeown et al., U.S. Pat. No. 5,603,920, Feb. 18, 1997, and U.S. Pat. No. 5,716,601, Feb. 10, 1998, both to Rice, and U.S. Pat. No. 6,740,311, May 25, 2004 to White et al.

A need exists for an abrasive system that has good compatibility with oral care actives and key dentifrice components, while providing effective and safe cleaning and polishing of dental tissue. In addition, there exists a continuing need for abrasives that can produce superior cleaning and polishing at reduced costs. The fused silicas of the present invention may provide one or more of these advantages. Fused silicas wherein the particles are spherical may particularly provide these advantages. Therefore, the present invention relates to oral care compositions comprising fused silica, wherein at least 25% of the fused silica particles are spherical.

SUMMARY OF THE INVENTION

The present invention relates to oral care compositions comprising fused silica, wherein at least about 25% of the fused silica particles are spherical.

BRIEF DESCRIPTION OF DRAWINGS

FIG. 1 is a table of material properties of various fused and precipitated silicas.

FIG. 2 is a table of compatibility data for fused and precipitated silicas.

FIG. 3A is a table of sodium fluoride-based formulations of oral care compositions.

FIG. 3B is a table of PCR and RDA values for FIG. 3A compositions.

FIG. 4A is a table of stannous fluoride-based formulas of oral care compositions.

FIG. 4B is a table of PCR and RDA values for FIG. 4A compositions.

FIG. 5 is a table of cleaning and abrasivity of fused silica.

FIG. 7A is a table of composition formulas.

FIG. 7B is a table of stannous, zinc, and fluoride compatibility for FIG. 7A compositions.

FIG. 8 is a table of stannous compatibility as a function of silica load.

FIG. 9A is a table of formula compositions comprising peroxide and fused and precipitated silicas.

FIG. 9B is a table of peroxide compatibility for the FIG. 9A compositions.

FIG. 10A is a table of formula compositions comprising fused silica.

FIG. 10B is a table of cleaning and whitening performance for FIG. 10A compositions.

FIG. 11A is table of formula compositions containing fused and precipitated silicas.

FIG. 11B is a table of consumer perception data for FIG. 11A compositions.

FIG. 12 is a depiction of how FIGS. 12A and 12B fit together into a single table.

FIG. 12A is a first portion of a table of additional formula examples.

FIG. 12B is a second portion of a table of additional formula examples.

FIG. 13A is a table of formula examples.

FIG. 13B is a table of PCR and RDA values for FIG. 13A sodium fluoride based compositions.

FIG. 13C is a table of formula examples.

FIG. 13D is a table of RDA values for FIG. 13C stannous fluoride based compositions.

DETAILED DESCRIPTION OF THE INVENTION

Figure 6A:
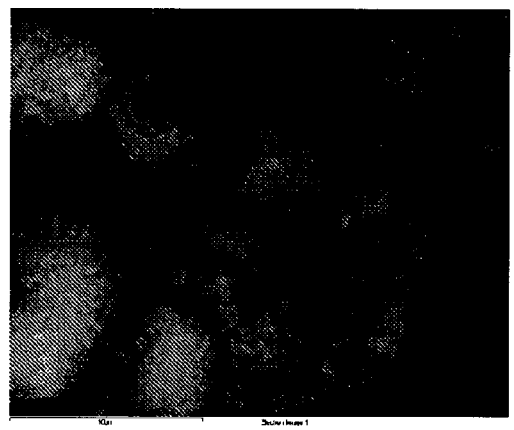
FIG. 6A A-I are SEM micrographs of precipitated and fused silica images.

While the specification concludes with claims that particularly point out and distinctly claim the invention, it is believed the present invention will be better understood from the following description.

DEFINITIONS

The term "orally acceptable carrier" as used herein means a suitable vehicle or ingredient, which can be used to form and/or apply the present compositions to the oral cavity in a safe and effective manner. Such vehicle may include materials such as fluoride ion sources, antibacterial agents, anticalculus agents, buffers, other abrasive materials, peroxide sources, alkali metal bicarbonate salts, thickening materials, humectants, water, surfactants, titanium dioxide, flavor system, sweetening agents, cooling agents, xylitol, coloring agents, other suitable materials, and mixtures thereof.

The term "comprising" as used herein means that steps and ingredients other than those specifically mentioned can be added. This term encompasses the terms "consisting of" and "consisting essentially of." The compositions of the present invention can comprise, consist of, and consist essentially of the essential elements and limitations of the invention described herein, as well as any of the additional or optional ingredients, components, steps, or limitations described herein.

The term "effective amount" as used herein means an amount of a compound or composition sufficient to induce a positive benefit, an oral health benefit, and/or an amount low enough to avoid serious side effects, i.e., to provide a reasonable benefit to risk ratio, within the sound judgment of a skilled artisan.

The term "oral composition" as used herein means a product that in the ordinary course of usage is retained in the oral cavity for a time sufficient to contact some or all of the dental surfaces and/or oral tissues for purposes of oral activity. The oral composition of the present invention may be in various forms including toothpaste, dentifrice, tooth gel, tooth powders, tablets, rinse, subgingival gel, foam, mouse, chewing gum, lipstick, sponge, floss, prophy paste, petrolatum gel, or denture product. The oral composition may also be incorporated onto strips or films for direct application or attachment to oral surfaces, or incorporated into floss.

The term "dentifrice" as used herein means paste, gel, powder, tablets, or liquid formulations, unless otherwise specified, that are used to clean the surfaces of the oral cavity.

The term "teeth" as used herein refers to natural teeth as well as artificial teeth or dental prosthesis.

The term "polymer" as used herein shall include materials whether made by polymerization of one type of monomer or made by two (i.e., copolymers) or more types of monomers.

The term "water soluble" as used herein means that the material is soluble in water in the present composition. In general, the material should be soluble at 25° C. at a concentration of 0.1% by weight of the water solvent, preferably at 1%, more preferably at 5%, more preferably at 15%.

The term "phase" as used herein means a mechanically separate, homogeneous part of a heterogeneous system.

The term "substantially non-hydrated" as used herein means that the material has a low number of surface hydroxyl groups or is substantially free of surface hydroxyl groups. It may also mean that the material contains less than about 5% total water (free or/and bound).

The term "majority" as used herein means the greater number or part; a number more than half the total.

The term "median" as used herein means the middle value in a distribution, above and below which lie an equal number of values.

All percentages, parts and ratios are based upon the total weight of the compositions of the present invention, unless otherwise specified. All such weights as they pertain to listed ingredients are based on the active level and, therefore, do not include solvents or by-products that may be included in commercially available materials, unless otherwise specified. The term "weight percent" may be denoted as "wt. %" herein.

All molecular weights as used herein are weight average molecular weights expressed as grams/mole, unless otherwise specified.

Fused Silica

Fused silica is a high-purity amorphous silicon dioxide. It is sometimes referred to as fused quartz, vitreous silica, silica glass, or quartz glass. Fused silica is a type of glass, which, typical of glasses, lacks long-range order in its atomic structure. But the optical and thermal properties of fused silica are unique from those of other glasses, as fused silica typically has more strength, thermal stability, and ultraviolet transparency. For these reasons, fused silica is known to be used in situations such as semiconductor fabrication and laboratory equipment.

The present invention utilizes fused silica in oral compositions, particularly in dentifrice compositions. While many current dentifrice compositions use silica as a thickening agent as well as an abrasive, the silicas typically used are precipitated silicas. Precipitated silicas are made by an aqueous precipitation or drying process. In contrast, fused silica is typically produced by melting high purity silica sand at very high temperatures, around 2000° C.

FIG. 1 is a table of material properties of various types of fused silica. For comparison, the same physical properties for some precipitated silicas are also shown. Some of the key material properties that distinguish fused silica from precipitated silica are shown, including BET surface area, loss on drying, loss on ignition, silanol density, bulk density, tapped density, oil absorption, and particle size distribution. Each of these material properties is discussed in more detail below.

The process of heating the silica to such high temperatures destroys the porosity and surface functionality of the silica. It produces a silica that is extremely hard and inert to most substances. The melting process also results in a low BET surface area, lower than that of precipitated silica. The BET surface area of fused silica ranges from about 1 $m^2/g$ to about 50 $m^2/g$, from about 2 $m^2/g$ to about 20 $m^2/g$, from about 2 $m^2/g$ to about 9 $m^2/g$, and from about 2 $m^2/g$ to about 5 $m^2/g$. By comparison, precipitated silicas typically have a BET surface area ranging between 30 $m^2/g$ and 80 $m^2/g$. BET surface area is determined by BET nitrogen absorption method of Brunaur et al., *J. Am. Chem. Soc.*, 60, 309 (1938). See also U.S. Pat. No. 7,255,852, issued Aug. 14, 2007 to Gallis.

Fused silica, relative to other types of silica, typically has a low amount of free or/and bound water. The amount of bound and free water in fused silica is typically less than about 10%. The amount of bound and free water in fused silica may be less than about 5%, or less than about 3%. Silicas with less than about 5% bound and free water may be considered substantially non-hydrated. The total bound and free water can be calculated by totaling two measurements, loss on drying (LOD) and loss on ignition (LOI). For loss on drying, performed first, a sample may be dried at 105° C. for two hours, the weight loss being the free water. For loss on ignition, the dried sample then may be heated for one hour at 1000° C., the weight loss being the bound water. The sum of the LOD and LOI represents the total bound and free water in the original sample. For example, following the described test method, fused silica TECO SIL 44CSS has a loss on drying of 0.1%, and a loss on ignition of 2.2%, for a sum of 2.3% total water. In comparison, a typical precipitated silica, Z-119, has a loss on drying of 6.1% and a loss on ignition of 5.1%, for a sum of 11.2% total water. (For another test method, see the United States Pharmacopeia-National Formulary (USP-NF), General Chapter 731, Loss on Drying and USP-NF, General Chapter 733, Loss on Ignition.)

Fused silica, relative to precipitated silica, has a low number of surface hydroxyl or silanol groups. The accounting of surface hydroxyl groups can be found by using nuclear magnetic resonance spectroscopy (nmr) to measure the silanol density of a particular silica. Silanols are compounds containing silicon atoms to which hydroxy substituents bond directly. When a solids nmr analysis is performed on various silicas, the silicon signal is enhanced by energy transfer from neighboring protons. The amount of signal enhancement depends on the silicon atom's proximity to protons found in the hydroxyl groups located at or near the surface. Therefore, the silanol density, stated as normalized silanol signal intensity (intensity/g), is a measure of surface hydroxyl concentration. The silanol density for fused silicas may be less than about 3000 intensity/g, in some embodiments less than about 2000 intensity/g, and commonly less than about 900 intensity/g. Fused silicas may contain an intensity/g of from about 10 to about 800 and typically from about 300 to about 700. For example, a sample of fused silica (TECO SIL 44CSS) has a silanol density of 574 intensity/g. A typical precipitated silica measures above 3000 intensity/g and typically above 3500 intensity/g. For example, Huber's Z-119 measures 3716 intensity/g. Test method for silanol density used solid state nmr with cross polarization with magic angle spinning (5 kHz) and high power gated proton decoupling and Varian Unity Plus-200 spectrometer with a 7 mm supersonic dual channel probe made by Doty Scientific. The relaxation delay was 4 seconds (s) and the contact time was 3 ms. Number of scans was between 8,000 and 14,000, and the experimental time frame was 10-14 hours per sample. Samples are weighed to 0.1 mg for normalization procedure. Spectra were plotted in absolute intensity mode and integrals were obtained in absolute intensity mode. Silanol density is measured by plotting and integrating spectra in absolute intensity mode.

The surface reactivity of silica, a reflection of the relative number of surface hydroxyls, may be measured by a silica's ability to absorb methyl red from a solution. This measures the relative number of silanols. The test is based on the fact that methyl red will selectively absorb on the reactive silanol sites of a silica surface. In some embodiments, the methyl red solution after exposure to fused silica may have an absorbance greater than the absorbance of a solution exposed to a typical precipitated silica. This is because the fused silica does not react as much with the methyl red solution as the precipitated silica. Typically, the fused silica will have a methyl red solution absorbance of 10% greater than a standard precipitated silica because the precipitated silica reacts more readily with the methyl red solution. The absorbance may be measured at 470 nm. Ten grams of 0.001% methyl red in benzene is added to 0.1 gram each of two silica samples and mixed for five minutes on a magnetic stirrer. The resulting slurries are centrifuged for five minutes at 12,000 rpms, and then the percent transmission at 470 nm is determined for each sample and averaged. See "Improving the Cationic Compatibility of Silica Abrasives Through the Use of Topochemical Reactions" by Gary Kelm, Nov. 1, 1974, in Iler, Ralph K., The Colloid Chemistry of Silica and Silicates, Cornell University Press, Ithaca, N.Y., 1955.

Without being bound by theory, it is believed that the fused silica, with its low BET specific surface area, low porosity, and low number of surface hydroxyl groups, is less reactive than precipitated silica. Consequently, the fused silica may adsorb less of other components, such as flavors, actives, or cations, leading to better availability for these other components. For example, dentifrices incorporating fused silica have superior stability and bioavailability for stannous, fluoride, zinc, other cationic antibacterials, and hydrogen peroxide. Fused silica formulated in a dentifrice composition may result in at least about 50%, 60%, 70%, 80%, or 90% compatibility with cations or other components. In some embodiments, the cation may be stannous.

In FIG. 2, the stannous and fluoride compatibility of various types of fused and precipitated silicas is shown. Stannous and fluoride compatibility was determined by adding 15% of silica into a sorbitol/water mixture containing 0.6% sodium gluconate and 0.454% stannous fluoride and mixed well. Each silica slurry sample was then placed on stability at 40° C. for 14 days, and then analyzed for stannous and fluoride. A measure of the concentration of soluble stannous and soluble zinc under normal tooth brushing conditions may be as follows: Prepare a 3:1 water to dentifrice (silica) slurry and centrifuge it to isolate a clear layer of supernatant. Dilute the supernatant in acid solution (nitric or hydrochloric acid) and analyze by inductively coupled plasma optical emission spectrometry. Percent compatibility is calculated by deducting the analyzed from initial values. A measure of the concentration of soluble fluoride under normal tooth brushing conditions may be as follows: Prepare a 3:1 water to dentifrice (silica) slurry and centrifuge it to isolate a clear layer of supernatant. The supernatant is analyzed for fluoride by either fluoride electrode (after mixing 1:1 with a TISAB buffer) or diluted with hydroxide solution and analyzed by ion chromatography with conductivity detection. Percent compatibility is calculated by deducting the analyzed from initial values. In general, cation compatibility may be determined by the "% CPC compatibility test" disclosed in U.S. Pat. No. 7,255,852.

There are numerous other characteristic differences between fused silica and precipitated silicas besides compatibility and concentration of surface hydroxyls. For example, fused silica is denser and less porous. The bulk density of fused silica is typically higher than 0.45 g/ml, and may be from about 0.45 g/ml to about 0.80 g/ml, while the bulk density of precipitated silicas is at most about 0.40 g/ml. The tapped density of fused silica is typically higher than 0.6 g/ml, and may be from about 0.8 g/ml to about 1.30 g/ml, while the tapped density of precipitated silicas is at most 0.55 g/ml. Bulk density and tapped density can be measured by following the methods in the USP-NF, General Chapter 616, Bulk Density and Tapped Density. For bulk density, method 1, Measurement in a Graduated Cylinder may be used; for tapped density, method 2, which uses a mechanical tapper, may be followed. Bulk density and tapped density represent mass to volume ratios of particles (multiple particles confined in a given space), and reflect trapped air, porosity, and how particles fit together in a given space. A true or intrinsic density of a particle (mass to volume ratio of a single particle) for fused silica is from about 2.1 $g/cm^3$ to 2.2 $g/cm^3$, while the true or intrinsic density of precipitated silicas is at most about 2.0 $g/cm^3$. Similarly, fused silica's specific gravity may be from about 2.1 to 2.2, while the specific gravity of precipitated silicas may be at most about 2.0. The difference in density may have a significant effect during the manufacture of a dentifrice product, for example, where fused silica's higher density reduces or removes the processing step of deaeration, which may result in shorter batch cycle times.

Fused silica has comparatively low water and oil absorption, measurements that correlate well with BET specific surface area. Water absorption for fused silica, meaning the amount of water that it can absorb while maintaining a powder consistency, is less than about 80 g/100 g, optionally less than about 70 g/100 g, about 60 g/100 g, or about 50 g/100 g. The water absorption for fused silica can be even lower, in the range of less than about 40 g/100 g, optionally less than about 30 g/100 g, and may be from about 2 g/100 g to about 30 g/100 g. For precipitated silicas, water absorption is typically about 90 g/100 g. Water absorption is measured using the J.M Huber Corp. standard evaluation method, S.E.M No. 5,140, Aug. 10, 2004). Oil absorption for fused silica is less than about 75 ml dibutyl phthalate/100 g fused silica, and may be less than about 60 ml dibutyl phthalate/100 g fused silica. Oil absorption may range from about 10 ml dibutyl phthalate/100 g fused silica to about 50 ml dibutyl phthalate/100 g fused silica, and it may be desired to be from about 15 ml dibutyl phthalate/100 g fused silica to about 45 ml dibutyl phthalate/100 g fused silica. For precipitated silicas, oil absorption is typically about 100 ml dibutyl phthalate/100 g precipitated silica. (Oil absorption is measured according to the method described in U.S. Patent Application 2007/0001037A1, published Jan. 4, 2007.

Due to its relatively low water absorption, the fused silica may be made into a slurry during processing, ultimately allowing quicker processing and faster batch times. In general, to create a precipitated silica slurry would typically require at least about 50% water. Therefore, it would not be practical to use a precipitated silica slurry in the manufacture of oral compositions. But because of the inertness, or lack of porosity of fused silica, reflected in fused silica's relatively low water absorption, fused silica slurries can be made in which water comprises less than about 30% in some embodiments, or less than 40% in some embodiments. Some embodiments may be a method of making an oral care composition comprising the addition of a fused silica slurry. In some embodiments, the fused silica slurry comprises a binder. This may help keep the fused silica suspended in the slurry, especially if there is a high water amount. It may also allow the binder more time to hydrate. In some embodiments, the binder is selected from the group consisting of carboxyvinyl polymers, carrageenan, hydroxyethyl cellulose, water soluble salts of cellulose ethers such as sodium carboxymethylcellulose, cross-linked carboxymethylcellulose, sodium hydroxyethyl cellulose, cross-linked starch, natural gums such as gum karaya, xanthan gum, gum arabic, and gum tragacanth, magnesium aluminum silicate, silica, alkylated polyacrylates, alkylated cross linked polyacrylates, and mixtures thereof. The fused silica slurry may be premixed. In some embodiments, the fused silica slurry may be flowable or pumpable. In some embodiments, the fused silica slurry may further comprise a preservative, for example benzoic acid, sodium benzoate, sorbic acid or parabens may be used, at less than about 1%.

Fused silica typically has much less conductivity than precipitated silica. Conductivity is an indirect measure of dissolved electrolytes, and precipitated silica can not be made without producing soluble electrolytes. So while precipitated silica ranges from about 900-1600 micro siemens/cm (based on 5% dispersion in deionized water), fused silica measures less than about 10 micro Siemens/cm (measurements made using an Orion 3 Star Benchtop Conductivity Meter available from Thermo Electron Corporation).

The pH of fused silica may range from about 5 to about 8, while the pH of precipitated silicas is typically from about 7 to about 8. pH is determined according to U.S. patent application 2007/0001037A1, published Jan. 4, 2007.

The refractive index, a measure of light transmission, is typically higher for fused silica than it is for precipitated silica. Put in a sorbitol/water mixture, fused silica measures a refractive index of at least about 1.45, while precipitated silicas measures from 1.44 to 1.448. A higher refractive index may allow the making of clear gels easier. Refractive index is determined using the method disclosed in U.S. patent application 2006/0110307A1, published May 25, 2006.

Fused silica typically has a Mohs hardness greater than about 6, greater than about 6.5, and greater than about 7. Precipitated silicas are not as hard, typically having a Mohs hardness of 5.5-6.

Another distinction between fused and precipitated silica is purity, with fused silica having a higher purity than precipitated. The percent of silica, by weight, in fused silica may be greater than about 97%, about 97.5%, about 98%, about 98.5%, in some embodiments greater than about 99%, and in some embodiments greater than about 99.5%. For precipitated silica, the percent of silica, by weight, is typically only about 90%. These purity measurements include water as an impurity, and may be calculated using the LOD and LOI methods described previously.

Depending on the supplier, impurities other than water may include metal ions and salts, among other materials. In general, for precipitated silicas, impurities other than water are mostly sodium sulfate. Precipitated silicas will typically have from about 0.5% to 2.0% sodium sulfate. Fused silica typically does not contain any sodium sulfate, or has less than 0.4%. Purity levels that do not include water may be determined by referring to the USP-NF Dental Silica Silicon Monograph, as follows: Purity is the combined results of the Assay (silicon dioxide) and Sodium sulfate tests. For Assay Transfer about 1 g of Silica Gel to a tared platinum dish, ignite at 1000° C. for 1 hour, cool in a desiccator, and weigh. Carefully wet with water, and add about 10 mL of hydrofluoric acid, in small increments. Evaporate on a steam bath to dryness, and cool. Add about 10 mL of hydrofluoric acid and about 0.5 mL of sulfuric acid, and evaporate to dryness. Slowly increase the temperature until all of the acids have been volatilized, and ignite at 1000° C. Cool in a desiccator, and weigh. The difference between the final weight and the weight of the initially ignited portion represents the weight of SiO2. Sodium sulfate—Transfer about 1 g of Dental-Type Silica, accurately weighed, to a platinum dish, wet with a few drops of water, add 15 mL of perchloric acid, and place the dish on a hot plate. Add 10 mL of hydrofluoric acid. Heat until copious fumes are evolved. Add 5 mL of hydrofluoric acid, and again heat to copious fumes. Add about 5 mL of boric acid solution (1 in 25), and heat to fumes. Cool, and transfer the residue to a 400-mL beaker with the aid of 10 mL of hydrochloric acid. Adjust the volume with water to about 300 mL, and bring to boiling on a hot plate. Add 20 mL of hot barium chloride TS. Keep the beaker on the hot plate for 2 hours, maintaining the volume above 200 mL. After cooling, transfer the precipitate and solution to a dried, tared 0.8-μm porosity filter crucible. Wash the filter and precipitate 8 times with hot water, dry the crucible at 105° C. for 1 hour, and weigh. The weight, multiplied by 0.6085, is the sodium sulfate content of the amount of specimen taken. Not more than 4.0% is found. Purity may also be determined through use of standard analytical techniques, such as atomic absorption spectroscopy or through elemental analysis.

The unique surface morphology of fused silica may result in more favorable PCR/RDA ratios. The Pellicle Cleaning Ratio (PCR) of the fused silica of the present invention, which is a measure of the cleaning characteristics of a dentifrice, ranges from about 70 to about 200 and preferably from about 80 to about 200. The Radioactive Dentine Abrasion (RDA) of the inventive silica, which is a measure of the abrasiveness of the fused silica when incorporated into a dentifrice, is less than about 250, and may range from about 100 to about 230.

FIG. 3(a) shows sodium fluoride-based formula compositions comprising various fused and precipitated silicas. FIG. 3(b) shows the corresponding PCR and RDA values. FIG. 4(a) shows stannous fluoride-based formula compositions comprising various fused and precipitated silicas. FIG. 4(b) shows the corresponding PCR and RDA values. The PCR values are determined by the method discussed in "In Vitro Removal of Stain with Dentifrice," G. K. Stookey, et al., *J. Dental Res.*, 61, 1236-9, 1982. The RDA values are determined according to the method set forth by Hefferren, *Journal of Dental Research*, July-August 1976, pp. 563-573, and described in Wason, U.S. Pat. Nos. 4,340,583, 4,420,312, and 4,421,527. RDA values may also be determined by the ADA recommended procedure for determination of dentifrice abrasivity. The PCR/RDA ratio of the fused silica, when incorporated into a dentifrice, may be greater than 1, indicating that the dentifrice is providing effective pellicle cleaning without too much abrasivity. The PCR/RDA ratio may also be at least about 0.5. The PCR/RDA ratio is a function of the particle size, shape, texture, hardness, and concentration.

FIG. 5 is a table of PCR and RDA data for various amounts of silica, both fused and precipitated. It demonstrates that fused silica (TS10 and TS44CSS) can have superior cleaning capability (PCR) in comparison to precipitated silicas (Z119 and Z109). The data shows that an oral composition with 5% fused silica may clean better than an oral composition with 10% of precipitated silica. In addition, the data demonstrates that fused silica can provide this cleaning while still being within acceptable abrasivity levels (RDA).

The shape of the particles of fused silica may be classified as either angular or spherical, or a combination of shapes, depending on the type of manufacturing process. Additionally, the fused silica may also be milled to reduce particle size. Spherical particles include any particle where the whole particle is mostly rounded or elliptical in shape. Angular particles include any particle that is not spherical, including polyhedral shapes. The angular particles may have some rounded edges, some or all sharp edges, some or all jagged edges, or a combination. The particle shape of the fused silica can impact its abrasivity. For example, at the same particle size, spherical fused silica may have a lower radioactive dentin abrasion (RDA) than that of angular fused silica. Consequently, it may be possible to optimize cleaning capability while not increasing abrasivity. Or, as another example, a prophy paste or a paste to be used weekly could comprise an angular fused silica with a large particle size.

Compositions that comprise spherical fused silica, that is, wherein at least 25% of the fused silica particles are spherical, have certain advantages. Due to the rounded edges, the spherical fused silica may be less abrasive. This means that the PCR to RDA ratio can be improved while still providing good cleaning. Also, spherical fused silica may be used at higher levels without being too abrasive. The spherical fused silica may also be used in combination with the angular fused silica, or silica wherein at least about 25% of the particles are angular. This could help lower costs, while still delivering good cleaning with acceptable abrasivity. In embodiments that have both angular and spherical fused silica, the amount of angular fused silica may be from about 1% to about 10%, by weight of the composition.

In some embodiments wherein at least 25% of the fused silica particles are spherical, the RDA may be less than 150, in other embodiments less than 120. In some embodiments wherein at least 25% of the fused silica particles are spherical, the PCR to RDA ratio may be at least about 0.7, at least about 0.8, at least about 0.9, or at least about 1.0. In some embodiments, the amount of fused silica may be from about 20% to about 50%, by weight of the composition, and in those embodiments, the composition may have an RDA value of less than 170. In some of those same embodiments, the median particle size of the fused silica may be from about 3.0 microns to about 15.0 microns.

Examples of spherical fused silicas include SPHERON P1500 and SPHERONN 2000R, made by Japanese Glass Company, and SUN-SIL 130NP.

Importantly, fused silica particles generally do not form as many aggregated clusters as precipitated silicas do and typically do not form aggregate clusters as easily as precipitated silicas do. In some embodiments, the majority of fused silica particles do not form aggregated clusters. In contrast, precipitated silicas generally form aggregated clusters of irregularly shaped submicron primary particles. A precipitated silica may be treated or coated which may increase or decrease the amount of aggregation. The particle shape of both fused and precipitated silica may be determined using a scanning electron microscope (SEM).

Figure 6B:
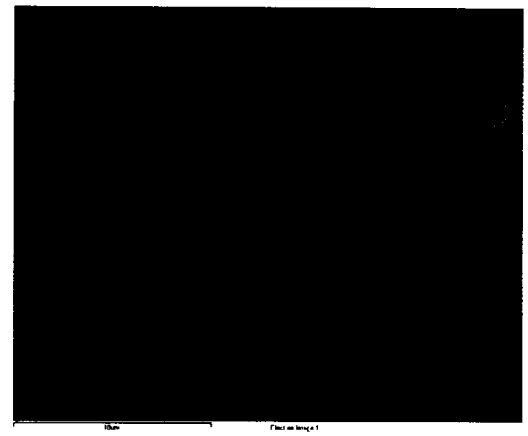
Figure 6C:
Figure 6D:
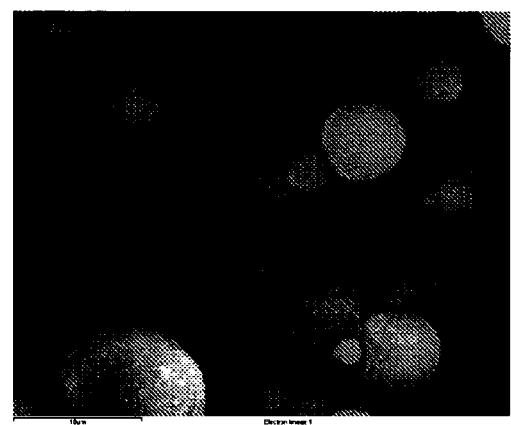
Figure 6E:
Figure 6F:
Figure 6G:
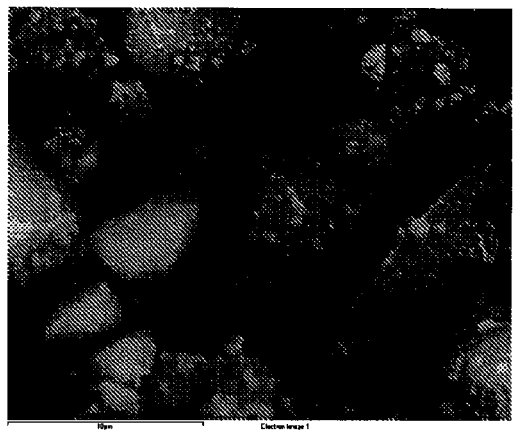
Figure 6H:
Figure 6I:
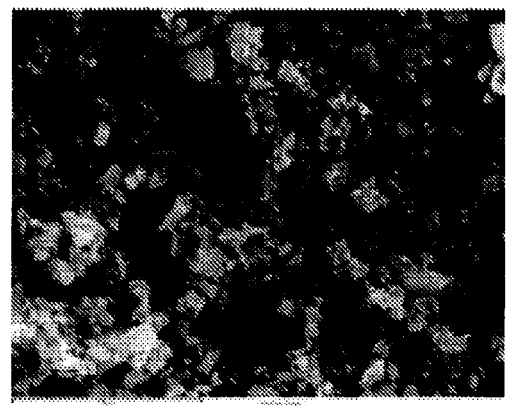

FIG. 6, (a)-(i), are SEM micrographs of precipitated and fused silicas at 3000× magnification. Samples were sputter coated with gold using EMS575X Peltier cooled Sputter coater. SEM images of the sample surface were obtained using a JEOL JSM-6100. The SEM was operated at 20 kV, 14 mm WD, and 1500× and 3000× magnification.

Micrographs (a) and (b), of precipitated silicas Z-109 and Z-119, show irregularly shaped-agglomerated particles. Particles appear to be made of agglomerated smaller particles loosely packed together. Micrographs (c) and (d), which are fused silicas Spheron P1500 and Spheron N-2000R, show regularly shaped spheroid particles. That is, each particle, for the most part, is shaped like a sphere. And micrographs (e), (f), (g), (h), and (i), which are fused silicas 325F, RG5, RST 2500 DSO, Teco-Sil 44C, and Teco-Sil 44CSS, show irregularly shaped dense particles. Some particles may be agglomerated, tightly packed, while others appear to consist of a single mass. In general, this last set of fused silicas has particles that are irregularly shaped with defined and/or sharp edges, and could be considered angular.

In general, oral compositions, for example dentifrice, comprising fused silica may be distinguished from oral compositions comprising only precipitated silica by heating both compositions to ash at about 500° C. and comparing the samples. Heating to about 500° C. leaves only the abrasive, but is not hot enough to drive off the hydroxyl groups. The fused silica and precipitated silica may be distinguished via BET surface area or SEM analysis, as described above, or by XRD (x-ray scattering technique) analysis.

The median particle size of fused silicas of the present invention may range from about 1 micron to about 20 microns, from about 1 micron to about 15 microns, from about 2 microns to about 12 microns, from about 3 microns to about 10 microns, as measured by Malvern Laser Light Scattering Particle Sizing. Angular shaped particles may have a particle size (median D50) from about 5 to about 10 microns. It is preferred that the D90 (average size of 90% of particles) is less than about 50 microns, less than about 40 microns, less than about 30 microns, or less than about 25 microns. A low particle size of fused silica may give a sensitivity benefit, as the particles may block tubule openings. Particle size is determined using the methods disclosed in U.S. patent application 2007/0001037A1, published Jan. 4, 2007.

The size of fused silica particles can be controlled by the processing of the material. Precipitated silica will have a size based on the method of precipitation. While the particle size of some precipitated silicas overlap with those of fused silicas, typically precipitated silicas will have a bigger particle size. For example, precipitated silicas Z-109 and Z-119 range from about 6 microns to about 12 microns and from about 6 microns to about 14 microns, respectively. But it is important to note that if, for example, a fused silica and a precipitated silica have the same particle size, the fused silica's BET surface area will typically still be much lower than the precipitated silica's BET surface area due to the lack of porosity of the fused silica particle. So a fused silica having a similar particle size to that of a precipitated silica will be distinguishable from the precipitated silica and offer the improved cleaning and/or compatibility over the precipitated silica.

In some embodiments, the particle size of the fused silica may be optimized for cleaning. In some embodiments, the median particle size of the fused silica may be from about 3 microns to about 15 microns, wherein 90% of the particles have a particle size of about 50 microns or less. In other embodiments, the median particle size may be from about 5 microns to about 10 microns, wherein 90% of the particles have a particle size of about 30 microns or less. In other embodiments, the median particle size may be from about 5 microns to 10 microns, wherein 90% of the particles have a particle size of about 15 microns or less.

The fact that fused silica is harder than precipitated silica contributes to its ability to clean better. This means that fused silica of the same particle size and in the same amount as a precipitated silica will comparatively clean better. For example, the PCR for a fused silica composition may be at least about 10% greater than the PCR for a precipitated silica composition when the median particle size and silica levels are the same.

Fused silica's better cleaning capability leads to different formulation possibilities, some that maximize cleaning, some that improve cleaning while not increasing abrasivity, some that improve cleaning while decreasing abrasivity, or some formulations that are simply more cost effective because less abrasive is required to deliver acceptable cleaning. In some embodiments, an oral care composition comprising a fused silica abrasive may have a PCR of at least about 80, at least about 100, or at least about 120. In some embodiments, the ratio of PCR to RDA may be at least about 0.6, at least about 0.7, at least about 0.8, or at least about 0.9. In some embodiments, the composition may comprise less than about 20% fused silica, by weight of the composition. In some embodiments, the composition may comprise less than about 15% fused silica, by weight of the composition, and have a PCR of at least about 100, or may comprise less than about 10% fused silica, by weight of the composition, and have a PCR of at least about 100.

In some embodiments optimized for improved cleaning, at least about 80% of the fused silica particles may be angular. In other embodiments, the composition may further comprise precipitated silica. In still other embodiments, the composition may comprise a gel network. In some embodiments, the composition may comprise one or more of the following: anticaries agent, antierosion agent, antibacterial agent, anticalculus agent, antihypersensitivity agent, anti-inflammatory agent, antiplaque agent, antigingivitis agent, antimalodor agent, and/or an antistain agent. In some embodiments, the composition may comprise an additional abrasive material, including, but not limited to precipitated silica, calcium carbonate, dicalcium phosphate dihydrate, calcium phosphate, perlite, pumice, calcium pyrophosphate, nanodiamonds, surface treated and de-hydrated precipitated silica, and mixtures thereof. Some embodiments may be a method of cleaning subject's teeth and oral cavity by using an oral care composition comprising a fused silica abrasive in an orally acceptable carrier, wherein the fused silica abrasive has a median particle size from about 3 microns to about 15 microns, and wherein 90% of the particles have a particle size of about 50 microns or less.

In some embodiments, the particle size of the fused silica may be reduced to focus on polishing and anti-sensitivity benefits. In some embodiments, the fused silica may have a median particle size of from about 0.25 micron to about 5.0 microns, from about 2.0 microns to about 4.0 microns, or from about 1.0 micron to about 2.5 microns. In some embodiments, 10% of the fused silica particles may have a particle size of about 2.0 microns or less. In some embodiments, 90% of the fused silica particles may have a particle size of about 4.0 microns or less. In some embodiments, particles may have a median particle size that is no greater than the average diameter of a mammalian dentin tubule, such that one or more particles is/are capable of becoming lodged within the tubule, thereby effecting a reduction or elimination of perceived tooth sensitivity. Dentinal tubules are structures that span the entire thickness of dentin and form as a result of the mechanism of dentin formation. From the outer surface of the dentin to the area nearest the pulp, these tubules follow an S-shaped path. The diameter and density of the tubules are greatest near the pulp. Tapering from the inner to the outermost surface, they have a diameter of 2.5 microns near the pulp, 1.2 microns in the middle of the dentin, and 0.9 microns at the dentino-enamel junction. Their density is 59,000 to 76,000 per square millimeter near the pulp, whereas the density is only half as much near the enamel.

To enhance the anti-sensitivity benefit of a small particle size, compositions may further comprise additional anti-sensitivity agents such as, for example, tubule blocking agents and/or desensitivity agents. Tubule blocking agents may be selected from the group consisting of stannous ion source, strontium ion source, calcium ion source, phosphorus ion source, aluminum ion source, magnesium ion source, amino acids, bioglasses, nanoparticulates, polycarboxylates, Gantrez, and mixtures thereof. The amino acids may be basic amino acids, and a basic amino acid may be arginine. Nanoparticulates may be selected from the group consisting of nanohydroxy apatite, nanotitanium dioxide, nano metal oxides, and mixtures thereof. The desensitivity agent may be a potassium salt selected from the group consisting of potassium fluoride, potassium citrate, potassium nitrate, potassium chloride, and mixtures thereof. Some embodiments may be a method of reducing hypersensitivity of the teeth by administering to a subject in need an oral care composition comprising a fused silica, wherein the fused silica has a median particle size of 0.25 micron to about 5.0 microns. Some embodiments may be a method of polishing the teeth by administering to a subject an oral care composition comprising a fused silica, wherein the fused silica has a median particle size of 0.25 micron to about 5.0 microns.

In other embodiments, the particle size may be relatively large to be part of a prophy paste or some other non-daily use paste. In some embodiments, the fused silica may have a median particle size of at least about 7 microns and wherein the composition has a PCR of at least about 100. In other embodiments, the median particle size may be from about 7 microns to about 20 microns. In some embodiments with the median particle size at least about 7 microns, an additional abrasive may be used, selected from the group consisting of pumice, perlite, precipitated silica, calcium carbonate, rice hull silica, silica gels, aluminas, phosphates including orthophosphates, polymetaphosphates, pyrophosphates, other inorganic particulates, and mixtures thereof. In embodiments with the larger particle size, the fused silica may be from about 1% to about 10%, by weight of the composition. Some embodiments may be essentially free of surfactant, fluoride, or any oral care active. Some embodiments may have a flavoring agent. Some embodiments are methods of cleaning and polishing dental enamel by comprising an oral care composition wherein the median particle size is at least about 7 microns and the composition has a PCR of at least about 100.

Fused silica may be made by melting silica (quartz or sand) at 2000° C. After cooling into ingots or pellets, the material is milled. Milling techniques vary, but some examples include jet milling, hammer milling, or ball milling. Ball milling may result in more rounded edges to the particles, while jet milling may result in more sharp or angular edges. Fused silica may be made by the process disclosed in U.S. Pat. No. 5,004,488, Mehrotra and Barker, 1991. Fused silica may also be made from a silicon-rich chemical precursor usually using a continuous flame hydrolysis process that involves chemical gasification of silicon, oxidation of this gas to silicon dioxide, and thermal fusion of the resulting dust. This process can produce spherical fused silica, but can be more expensive. While the making of precipitated silica is a chemical process, the making of fused silica is a natural process. The production of fused silica produces less waste and offers better sustainability benefits.

In some embodiments of the present invention, there may be multiple types of fused silica. For example, fused silica may be made by melting the silica at even higher temperatures, such as 4000° C. Such fused silicas may have a different particle size or surface morphology, but still maintain the benefits discussed above, including low reactivity, due to the relatively low surface hydroxyl concentration and/or low BET specific surface area.

Precipitated, or hydrated, silicas may be made by dissolving silica (sand) using sodium hydroxide and precipitating by adding sulfuric acid. After washing and drying, the material is then milled. Such precipitated silicas may be made by the process disclosed in U.S. Pat. No. 6,740,311, White, 2004. Precipitated and other silicas are described in more detail in the Handbook of Porous Solids, edited by Ferdi Schuth, Kenneth S. W. Sing and Jens Weitkamp, chapter 4.7.1.1.1, called Formation of Silica Sols, Gels, and Powders, and in Cosmetic Properties and Structure of Fine-Particle Synthetic Precipitated Silicas, S. K. Wason, *Journal of Soc. Cosmetic Chem.*, vol. 29, (1978), pp 497-521.

The amount of fused silica used in the present invention may be from about 1%, 2%, 5%, 7%, 10%, 12%, 15%, 20%, 25%, 30%, 35%, 40%, 45%, 50% to about 5%, 7%, 10%, 12%, 15%, 20%, 25%, 30%, 35%, 40%, 45%, 50%, 55%, 60%, 65%, or 70%, or any combination thereof. The fused silicas of the present invention may be used alone or with other abrasives. A composition may comprise more than one type of fused silica. One type of abrasive that may be used with fused silica is a precipitated silica. The total abrasive in the compositions described herein is generally present at a level of from about 5% to about 70%, by weight of the composition. Preferably, dentifrice compositions contain from about 5% to about 50% of total abrasive, by weight of the composition. For combinations of fused silica with precipitated silicas, the fused silica may be from about 1% to about 99%, by weight of the total abrasive. The precipitated silica or silicas may be from about 1% to about 99% by weight of the total abrasive. In some embodiments, small amounts of fused silica may be used, from about 1% to about 10%, or from about 2% to about 5%.

The fused silica may be used in combination with inorganic particulates that have been treated with non-ionic surfactants such as ethoxylated and non-ethoxylated fatty alcohols, acid and esters. One example of such non-ionic surfactant is PEG 40 hydrogenated Castor oil. In general, the oral care compositions of the present invention may be used with additional abrasive material, such as one or more selected from the group consisting of precipitated silica, calcium carbonate, rice hull silica, silica gels, aluminums, aluminum silicates, phosphates including orthophosphates, polymetaphosphates, pyrophosphates, other inorganic particulates, dicalcium phosphate dihydrate, calcium phosphate, perlite, pumice, calcium pyrophosphate, nanodiamonds, surface treated and de-hydrated precipitated silica, and mixtures thereof.

In some embodiments, the ratio of other abrasive to fused silica is greater than about 2 to 1, in some embodiments, greater than about 10 to 1. In some embodiments, the ratio is about 1 to 1. In some embodiments, the amount of fused silica, by weight of the composition, is from about 1% to about 10%. In some embodiments, the amount of fused silica, by weight of the abrasive combination, is from about 2% to about 25%. In one embodiment, the other abrasive is calcium carbonate. In some embodiments, the amount of calcium carbonate, by weight of the composition, is from about 20% to about 60%. In some embodiments, the amount of calcium carbonate, by weight of the composition, is from about 20% to about 60%. In another embodiment, an additional abrasive may comprise at least one precipitated silica. The precipitated silica abrasive may comprise from about 5% to about 40%, by weight of the combination. The amount of fused silica in the abrasive combination may comprise from about 1% to about 10%, by weight of the composition. In some embodiments, the composition comprising an abrasive combination may have a PCR of at least about 80, about 100, or about 120, or an RDA of less than about 150 or less than about 200.

To further increase cation availability in compositions, the fused silicas of the present invention may be used in combination with treated precipitated silicas, such as surface-modified precipitated silica, dehydrated precipitated silica, or precipitated silicas with reduced porosity, reduced surface hydroxyl groups, or small surface areas that have better cation compatibility vs. regular precipitated silicas. But it is emphasized that these particular precipitated silicas are surface-treated in an attempt to reduce surface hydroxyls and to improve properties such as low porosity or cationic compatibility, but that they would still be considered precipitated silicas. (See, for example, U.S. Pat. No. 7,255,852, U.S. Pat. No. 7,438,895, WO 9323007, and WO 9406868.) That is, they are silicas produced by a wet process. Water is added during the manufacturing process and then later removed. That remains true even for a precipitated silica that may be heated to very high temperatures in an attempt to remove hydroxyl groups. In contrast, fused silica, although it could be, does not need to be surface-treated or treated at all. Fused silica is manufactured without any water, but by heating only. This heating process can more effectively reduce surface hydroxyls than most precipitated processes can.

Other abrasive polishing materials may include silica gels, rice hull silica, aluminas, phosphates including orthophosphates, polymetaphosphates, and pyrophosphates, and mixtures thereof. Specific examples include dicalcium orthophosphate dihydrate, calcium pyrophosphate, tricalcium phosphate, calcium polymetaphosphate, insoluble sodium polymetaphosphate, hydrated alumina, beta calcium pyrophosphate, calcium carbonate, and resinous abrasive materials such as particulate condensation products of urea and formaldehyde, and others such as disclosed by Cooley et al in U.S. Pat. No. 3,070,510, issued Dec. 25, 1962.

The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975. Examples are the silica xerogels marketed under the trade name "Syloid" by the W.R. Grace & Company, Davison Chemical Division. Also there are the precipitated silica materials such as those marketed by the J. M. Huber Corporation under the trade name, "Zeodent", particularly the silicas carrying the designation "Zeodent 109" (Z-109) and "Zeodent 119" (Z-119). Other precipitated silicas commercially available and comparable to Z-109 and Z-119 include, for example, Tixosil 63, Tixosil 73, and Tixosil 103, all made by Rhodia, Huber silicas Z-103, Z-113, and Z-124, OSC DA, made by OSC in Taiwan, and ABSIL-200 and ABSIL-HC, made by Madhu Silica. Of these commercially available precipitated silicas, Tixosil 73 is the most similar to Z-119. The present precipitated silica abrasives may be used in combination with fused silica and other abrasives.

The types of precipitated silica dental abrasives that may be mixed with the fused silica of the present invention are described in more detail in Wason, U.S. Pat. No. 4,340,583, issued Jul. 29, 1982. Precipitated silica abrasives are also described in Rice, U.S. Pat. Nos. 5,589,160; 5,603,920; 5,651,958; 5,658,553; and 5,716,601.

One suitable type of fused silica is Teco-Sil 44CSS, which is available from C-E Minerals Products. Also available from C-E Minerals Products are fused silicas designated as Teco-Sil 44C, Teco-Sil T10, and TecoSpere A. Other suitable fused silicas include R61000, available from Jiangsu Kaida Silica and Spheron N-2000R and Spheron P1500, available from JGC, Japanese Glass Company. Others include RST 2500, RG 1500, and RG 5, available from Lianyungang Ristar Electronic Materials, SO-C5 and SO-C4, available from Adamatech, Fuserex AS-1, available from Tatsumori, FS 30 and FS-2DC, available from Denki Kagaku Kogyou, Min-Sil 325F, available from Minco, and Sunsil-130NP, available from Sunjin, and a fused silica from Shin-Etsu.

The CAS# for some types of fused silica is 60676-86-0. The CAS# for hydrated silica is 7631-86-9. The INCI name for fused silica is "fused silica", while the INCI name for precipitated silicas is "hydrated silica". The silicas of the present invention do not include silicates, and the fused silicas of the present invention do not include fused silicates.

Orally-Acceptable Carrier

The carrier for the components of the present compositions may be any orally-acceptable vehicle suitable for use in the oral cavity. The carrier may comprise suitable cosmetic and/or therapeutic actives. Such actives include any material that is generally considered safe for use in the oral cavity and that provides changes to the overall appearance and/or health of the oral cavity, including, but not limited to, anti-calculus agents, fluoride ion sources, stannous ion sources, whitening agents, anti-microbial, anti-malodor agents, anti-sensitivity agents, anti-erosion agents, anti-caries agents, anti-plaque agents, anti-inflammatory agents, nutrients, antioxidants, anti-viral agents, analgesic and anesthetic agents, H-2 antagonists, and mixtures thereof. When present, the level of cosmetic and/or therapeutic active in the oral care composition is, in one embodiment from about 0.001% to about 90%, in another embodiment from about 0.01% to about 50%, and in another embodiment from about 0.1% to about 30%, by weight of the oral care composition.

Actives

One of the advantages of fused silica is its compatibility with other materials, particularly materials that are reactive and can loose efficacy such as actives. Because fused silica does not react as much with actives as compared to precipitated silica and other traditional abrasives, less of the active can be used with the same efficacy. If the active has any potential aesthetic negatives such an unpleasant or strong taste, astringency, staining, or other negative aesthetic, the lower amount of active may be preferred. Additionally, the use of less active for the same or similar efficacy is a cost savings. Alternatively, if the same amount of active as used as traditionally used, the active would have higher efficacy as more of it is available to provide the benefit. Because the fused silica is slightly harder than traditional abrasives such as precipitated silica, the fused silica may also remove more stain and/or clean better.

Actives include but are not limited to antibacterial actives, antiplaque agents, anticaries agents, antisensitivity agents, antierosion agents, oxidizing agents, anti-inflammatory agents, anticalculus agents, nutrients, antioxidants, analgesic agents, anesthetic agents, H-1 and H-2 antagonists, antiviral actives, and combinations thereof A material or ingredient may be categorized as more than one type of materials. Such as an antioxidant may also be an antiplaque and antibacterial active. Examples of suitable actives include stannous fluoride, sodium fluoride, essential oils, mono alkyl phosphates, hydrogen peroxide, CPC, chlorhexidine, Triclosan, and combinations thereof. The following is a non-limiting list of actives that may be used in the present invention.

Fluoride Ion

The present invention may comprise a safe and effective amount of a fluoride compound. The fluoride ion may be present in an amount sufficient to give a fluoride ion concentration in the composition at 25° C., and/or in one embodiment can be used at levels of from about 0.0025% to about 5.0% by weight, in another embodiment from about 0.005% to about 2.0% by weight, to provide anticaries effectiveness. A wide variety of fluoride ion-yielding materials can be employed as sources of soluble fluoride in the present compositions. Examples of suitable fluoride ion-yielding materials are disclosed in U.S. Pat. Nos. 3,535,421, and 3,678,154. Representative fluoride ion sources include: stannous fluoride, sodium fluoride, potassium fluoride, amine fluoride, sodium monofluorophosphate, zinc fluoride, and many others. In one embodiment the dentifrice composition comprises stannous fluoride or sodium fluoride, as well as mixtures thereof.

The pH of the oral composition may be from about 3 to about 10. The pH is typically measured as a slurry pH by methods known in the industry. Depending upon the actives used in the oral composition, a different pH may be desired. For formulations containing fluoride, it may be desired to have a pH slightly lower than typical dentifrices. Typical oral compositions with precipitated silica and fluoride have a pH high enough so that the fluoride in the formula does not form fluorosilicate and then react with the hydroxyl groups on the precipitated silica. Because the number of hydroxyl groups on fused silica is lower than the number of hydroxyl groups on precipitated silica, this is not an issue and the pH of the oral composition with fused silica can be lower.

Compositions containing fused silica and fluoride may have a pH of less than about 6.0 or less than about 5.5. The pH may be less than about 5.2 or about 5.0. It may be desired to have a pH of from about 3.5 to about 5 or from about 2.4 to about 4.8. The pH may be lower than 5.5 to allow higher fluoride uptake because more fluoride is available. The low pH may help to condition the tooth surface to accept more fluoride. For formulations containing peroxide and fused silica, the pH may be less than 5.5 or less than 4.5. A formulation with peroxide and fused silica may be from about 3.5 to about 4.0. For formulations comprising fused silica, stannous, and fluoride, it may be desired to have a pH of less than 5.0. A pH of less than 5.0 may enable more of the SnF3 stannous species to be formed.

Anticalculus Agent

Dentifrice compositions of the present invention may also comprise an anti-calculus agent, which in one embodiment may be present from about 0.05% to about 50%, by weight of the oral care composition, in another embodiment is from about 0.05% to about 25%, and in another embodiment is from about 0.1% to about 15%. The anti-calculus agent may be selected from the group consisting of polyphosphates (including pyrophosphates) and salts thereof polyamino propane sulfonic acid (AMPS) and salts thereof; polyolefin sulfonates and salts thereof; polyvinyl phosphates and salts thereof; polyolefin phosphates and salts thereof; diphosphonates and salts thereof; phosphonoalkane carboxylic acid and salts thereof; polyphosphonates and salts thereof; polyvinyl phosphonates and salts thereof; polyolefin phosphonates and salts thereof; polypeptides; and mixtures thereof; polycarboxylates and salts thereof; carboxy-substituted polymers; and mixtures thereof. In one embodiment, the polymeric polycarboxylates employed herein include those described in U.S. Pat. No. 5,032,386. An example of these polymers that is commercially available is Gantrez from International Specialty Products (ISP). In one embodiment, the salts are alkali metal or ammonium salts. Polyphosphates are generally employed as their wholly or partially neutralized water-soluble alkali metal salts such as potassium, sodium, ammonium salts, and mixtures thereof. The inorganic polyphosphate salts include alkali metal (e.g. sodium) tripolyphosphate, tetrapolyphosphate, dialkyl metal (e.g. disodium) diacid, trialkyl metal (e.g. trisodium) monoacid, potassium hydrogen phosphate, sodium hydrogen phosphate, and alkali metal (e.g. sodium) hexametaphosphate, and mixtures thereof. Polyphosphates larger than tetrapolyphosphate usually occur as amorphous glassy materials. In one embodiment the polyphosphates are those manufactured by FMC Corporation, which are commercially known as Sodaphos (n≈6), Hexaphos (n≈13), and Glass H (n≈21, sodium hexametaphosphate), and mixtures thereof. The pyrophosphate salts useful in the present invention include, alkali metal pyrophosphates, di-, tri-, and mono-potassium or sodium pyrophosphates, dialkali metal pyrophosphate salts, tetraalkali metal pyrophosphate salts, and mixtures thereof. In one embodiment the pyrophosphate salt is selected from the group consisting of trisodium pyrophosphate, disodium dihydrogen pyrophosphate ($Na_2H_2P_2O_7$), dipotassium pyrophosphate, tetrasodium pyrophosphate ($Na_4P_2O_7$), tetrapotassium pyrophosphate ($K_4P_2O_7$), and mixtures thereof. Polyolefin sulfonates include those wherein the olefin group contains 2 or more carbon atoms, and salts thereof. Polyolefin phosphonates include those wherein the olefin group contains 2 or more carbon atoms. Polyvinylphosphonates include polyvinylphosphonic acid. Diphosphonates and salts thereof include azocycloalkane-2,2-diphosphonic acids and salts thereof, ions of azocycloalkane-2,2-diphosphonic acids and salts thereof, azacyclohexane-2,2-diphosphonic acid, azacyclopentane-2,2-diphosphonic acid, N-methyl-azacyclopentane-2,3-diphosphonic acid, EHDP (ethane-1-hydroxy-1,1-diphosphonic acid), AHP (azacycloheptane-2,2-diphosphonic acid), ethane-1-amino-1,1-diphosphonate, dichloromethane-diphosphonate, etc. Phosphonoalkane carboxylic acid or their alkali metal salts include PPTA (phosphonopropane tricarboxylic acid), PBTA (phosphonobutane-1,2,4-tricarboxylic acid), each as acid or alkali metal salts. Polyolefin phosphates include those wherein the olefin group contains 2 or more carbon atoms. Polypeptides include polyaspartic and polyglutamic acids.

Stannous Ion

The oral compositions of the present invention may include a stannous ion source. As stated before, one of the advantages of fused silica is its compatibility with other materials, particularly materials that are reactive and can loose efficacy. Stannous ions are considered to be reactive so the use of stannous ions with a fused silica may have some important benefits. Because fused silica does not react as much with stannous as compared to precipitated silica and other traditional abrasives, less of the stannous can be used with the same efficacy. It has been reported that stannous may have potential aesthetic negatives such an unpleasant or strong taste, astringency, staining, or other negative aesthetics that make the stannous containing oral compositions less desirable for consumers. Therefore, using a lower amount of stannous may be preferred. Additionally, the use of less stannous for the same or similar efficacy is a cost savings. Alternatively, if the same amount of stannous is used as traditionally used, the stannous would have higher efficacy as more of it is available to provide the benefit. Because the fused silica is slightly harder than traditional abrasives such as precipitated silica, the fused silica may also remove more stain and/or clean better. It has also been discovered that stannous containing formulations may increase the strength of the teeth. Therefore, formulations containing stannous may have lower RDA scores than comparable formulations not containing stannous. The lower RDA scores may provide for a better PCR to RDA ratio as the fused silica is a good cleaning abrasive and the stannous provides for stronger teeth. The synergy provided with the combination of fused silica and stannous provides a highly efficacious, high cleaning formula for consumers.

The stannous ions may be provided from stannous fluoride and/or other stannous salts. Stannous fluoride has been found to help in the reduction of gingivitis, plaque, sensitivity, erosion, and in improved breath benefits. The stannous ions provided in a dentifrice composition will provide efficacy to a subject using the dentifrice composition. Although efficacy could include benefits other than the reduction in gingivitis, efficacy is defined as a noticeable amount of reduction in in situ plaque metabolism. Formulations providing such efficacy typically include stannous levels provided by stannous fluoride and/or other stannous salts ranging from about 50 ppm to about 15,000 ppm stannous ions in the total composition. The stannous ion is present in an amount of from about 1,000 ppm to about 10,000 ppm, in one embodiment from about 3,000 ppm to about 7,500 ppm. Other stannous salts include organic stannous carboxylates, such as stannous acetate, stannous gluconate, stannous oxalate, stannous malonate, stannous citrate, stannous ethylene glycoxide, stannous formate, stannous sulfate, stannous lactate, stannous tartrate, and the like. Other stannous ion sources include, stannous halides such as stannous chlorides, stannous bromide, stannous iodide and stannous chloride dihydride. In one embodiment the stannous ion source is stannous fluoride, in another embodiment stannous chloride dehydrate or trihydrate, or stannous gluconate. The combined stannous salts may be present in an amount of from about 0.001% to about 11%, by weight of the oral care compositions. The stannous salts may, in one embodiment, be present in an amount of from about 0.01% to about 7%, in another embodiment from about 0.1% to about 5%, and in another embodiment from about 1.5% to about 3%, by weight of the oral care composition.

Whitening Agent

A whitening agent may be included as an active in the present dentifrice compositions. The actives suitable for whitening are selected from the group consisting of alkali metal and alkaline earth metal peroxides, metal chlorites, perborates inclusive of mono and tetrahydrates, perphosphates, percarbonates, peroxyacids, and persulfates, such as ammonium, potassium, sodium and lithium persulfates, and combinations thereof. Suitable peroxide compounds include hydrogen peroxide, urea peroxide, calcium peroxide, carbamide peroxide, magnesium peroxide, zinc peroxide, strontium peroxide and mixtures thereof. In one embodiment the peroxide compound is carbamide peroxide. Suitable metal chlorites include calcium chlorite, barium chlorite, magnesium chlorite, lithium chlorite, sodium chlorite, and potassium chlorite. Additional whitening actives may be hypochlorite and chlorine dioxide. In one embodiment the chlorite is sodium chlorite. In another embodiment the percarbonate is sodium percarbonate. In one embodiment the persulfates are oxones. The level of these substances is dependent on the available oxygen or chlorine, respectively, that the molecule is capable of providing to bleach the stain. In one embodiment the whitening agents may be present at levels from about 0.01% to about 40%, in another embodiment from about 0.1% to about 20%, in another embodiment form about 0.5% to about 10%, and in another embodiment from about 4% to about 7%, by weight of the oral care composition.

Oxidizing Agent

The compositions of the invention may contain an oxidizing agent, such as a peroxide source. A peroxide source may comprise hydrogen peroxide, calcium peroxide, carbamide peroxide, or mixtures thereof. In some embodiments, the peroxide source is hydrogen peroxide. Other peroxide actives can include those that produce hydrogen peroxide when mixed with water, such as percarbonates, e.g., sodium percarbonates. In certain embodiments, the peroxide source may be in the same phase as a stannous ion source. In some embodiments, the composition comprises from about 0.01% to about 20% of a peroxide source, in other embodiments from about 0.1% to about 5%, in certain embodiments from about 0.2% to about 3%, and in another embodiment from about 0.3% to about 2.0% of a peroxide source, by weight of the oral composition. The peroxide source may be provided as free ions, salts, complexed, or encapsulated. It is desirable that the peroxide in the composition is stable. The peroxide may provide a reduction in staining, as measured by the Cycling Stain Test, or other relevant methods.

In addition to the optional ingredients detailed below, certain thickeners and flavors offer better compatibility with oxidizing agents such as peroxide. For example, in some embodiments, preferred thickening agents may be cross-linked polyvinylpyrrolidone, polyacrylates, alkylated polyacrylates, alkylated cross-linked polyacrylates, polymeric alkylated polyethers, carbomers, alkylated carbomers, gel networks, non-ionic polymeric thickeners, Sepinov EMT 10 (Seppic-hydroxyethyl acrylate/sodium acryloldimethyltaurate copolymer), Pure Thix 1450, 1442, HH (PEG 180 laureth-50/TMMP or Polyether 1-Rockwood Specialties), Structure 2001 (Akzo-Acrylates/Steareth-20 Itaconate copolymer), Structure 3001 (Akzo-Acrylates/Ceteth-20 Itaconate copolymer), Aculyn 28 (Dow Chemical/Rohm and Haas-Acrylates/Beheneth-25 Methacrylate Copolymer), Genopur 3500D (Clariant), Aculyn 33 (Dow Chemical/Rohm and Haas—Acrylates Copolymer), Aculyn 22 (Dow Chemical/Rohm and Haas-Acrylates/Steareth-20 Methacrylate Copolymer), Aculyn 46 (Dow Chemical/Rohm and Haas—PEG-150/Stearyl Alcohol/SMDI Copolymer), A500 (crosslinked carboxymethylcellulose—Hercules), Structure XL (hydroxypropyl starch phosphate-National Starch), and mixtures thereof.

Other suitable thickening agents may include polymeric sulfonic acids such as Aristoflex AVC, AVS, BLV and HMB (Clariant, acryloyldimethyltaurate polymers, co-polymers and cross polymers), Diaformer (Clariant, amineoxide methacrylate copolymer), Genapol (Clariant, fatty alcohol polyglycol ether and alkylated polyglycol ethoxylated fatty alcohol), fatty alcohols, ethoxylated fatty alcohols, high molecular weight non-ionic surfactants such as BRIJ 721 (Croda), and mixtures thereof.

Suitable flavor systems particularly compatible with peroxide include those discussed in US application 2007/0231278. In one embodiment, the flavor system comprises menthol in combination with at least one secondary cooling agent along with selected traditional flavor components that have been found to be relatively stable in the presence of peroxide. By "stable" herein is meant that the flavor character or profile does not significantly change or is consistent during the life of the product.

The present composition may comprise from about 0.04% to 1.5% total coolants (menthol+secondary coolant) with at least about 0.015% menthol by weight. Typically, the level of menthol in the final composition ranges from about 0.015% to about 1.0% and the level of secondary coolant(s) ranges from about 0.01% to about 0.5%. Preferably, the level of total coolants ranges from about 0.03% to about 0.6%.

Suitable secondary cooling agents or coolants to be used with menthol include a wide variety of materials such as carboxamides, ketals, diols, menthyl esters and mixtures thereof. Examples of secondary coolants in the present compositions are the paramenthan carboxamide agents such as N-ethyl-p-menthan-3-carboxamide, known commercially as "WS-3", N,2,3-trimethyl-2-isopropylbutanamide, known as "WS-23", and others in the series such as WS-5, WS-11, WS-14 and WS-30. Additional suitable coolants include 3-1-menthoxypropane-1,2-diol known as TK-10 manufactured by Takasago; menthone glycerol acetal known as MGA; menthyl esters such as menthyl acetate, menthyl acetoacetate, menthyl lactate known as Frescolat® supplied by Haarmann and Reimer, and monomenthyl succinate under the tradename Physcool from V. Mane. The terms menthol and menthyl as used herein include dextro- and levorotatory isomers of these compounds and racemic mixtures thereof. TK-10 is described in U.S. Pat. No. 4,459,425, Amano et al., issued Jul. 10, 1984. WS-3 and other agents are described in U.S. Pat. No. 4,136,163, Watson, et al., issued Jan. 23, 1979.

Traditional flavor components that have been found to be relatively stable in the presence of peroxide include methyl salicylate, ethyl salicylate, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, cinnamic aldehyde, octanol, octanal, decanol, decanal, phenylethyl alcohol, benzyl alcohol, benzaldehyde, alpha-terpineol, linalool, limonene, citral, vanillin, ethyl vanillin, propenyl guaethol, maltol, ethyl maltol, heliotropin, anethole, dihydroanethole, carvone, oxanone, menthone, β-damascenone, ionone, gamma decalactone, gamma nonalactone, gamma undecalactone, 4-hydroxy-2,5-dimethyl-3(2H)-furanone and mixtures thereof. Generally suitable flavoring agents are those containing structural features and functional groups that are less prone to oxidation by peroxide. These include derivatives of flavor chemicals that are saturated or contain stable aromatic rings or ester groups. Also suitable are flavor chemicals that may undergo some oxidation or degradation without resulting in a significant change in the flavor character or profile. Flavoring agents are generally used in the compositions at levels of from about 0.001% to about 5%, by weight of the composition.

In some embodiments, the pH of the composition may be from about 3.5 to about 5.5, which can provide additional stability for the oxidizing agent. In some embodiments, the composition may further comprise a stannous ion source. In some embodiments, the present invention may provide a method of reducing plaque, gingivitis, sensitivity, oral malodor, erosion, cavities, calculus, and staining by administering to a subject's oral cavity a composition comprising a fused silica and a peroxide. In some embodiments, the present invention provides a method of reducing plaque, gingivitis, sensitivity, oral malodor, erosion, cavities, calculus, and staining by administering to a subject's oral cavity first a composition not comprising a peroxide, and then a composition comprising a fused silica and a peroxide. In some embodiments, the composition may be in a single phase. In some embodiments, the composition may comprise an oxidizing agent and one or more of a fluoride ion source, zinc ion source, calcium ion source, phosphate ion source, potassium ion source, strontium ion source, aluminum ion source, magnesium ion source, or combinations thereof. In some embodiments, the composition may comprise an oxidizing agent and a chelant selected from the group consisting of polyphosphates, polycarboxylates, polyvinylpyrrolidone, polyvinyl alcohol, polymeric polyether, polymeric alkyl phosphate, copolymers of methyl vinyl ether and maleic anhydride, polyphosphonates and mixtures thereof. In some embodiments, the composition may comprise an oxidizing agent and an oral care active selected from the group consisting of antibacterial agents, antiplaque agents, anti-inflammatory agents, anticaries agents, anticalculus agents, antierosion agents, antimalodor agents, antisensitivity agents, nutrients, analgesic agents, anesthetic agents, H-1 and H-2 antagonists, antiviral actives, and combinations thereof. In some embodiments, the antibacterial agent may be selected from the group consisting of cetylpyridinium chloride, chlorhexiding, hexitidine, triclosan, metal ions, essential oils and mixtures thereof.

Antibacterial Agent

Antimicrobial agents may be included in the dentifrice compositions of the present invention. Such agents may include, but are not limited to cationic antibacterials, such as chlorhexidine, alexidine, hexetidine, benzalkonium chloride, domiphen bromide, cetylpyridinium chloride (CPC), tetradecylpyridinium chloride (TPC), N-tetradecyl-4-ethylpyridinium chloride (TDEPC), octenidine, bisbiguanides, zinc or stannous ion agents, grapefruit extract, and mixtures thereof. Other antibacterial and antimicrobial agents include, but are not limited to: 5-chloro-2-(2,4-dichlorophenoxy)-phenol, commonly referred to as triclosan; 8-hydroxyquinoline and its salts, copper II compounds, including, but not limited to, copper(II) chloride, copper(II) sulfate, copper(II) acetate, copper(II) fluoride and copper(II) hydroxide; phthalic acid and its salts including, but not limited to those disclosed in U.S. Pat. No. 4,994,262, including magnesium monopotassium phthalate; sanguinarine; salicylanilide; iodine; sulfonamides; phenolics; delmopinol, octapinol, and other piperidino derivatives; niacin preparations; nystatin; apple extract; thyme oil; thymol; antibiotics such as augmentin, amoxicillin, tetracycline, doxycycline, minocycline, metronidazole, neomycin, kanamycin, cetylpyridinium chloride, and clindamycin; analogs and salts of the above; methyl salicylate; hydrogen peroxide; metal salts of chlorite; pyrrolidone ethyl cocoyl arginate; lauroyl ethyl arginate monochlorohydrate; and mixtures of all of the above. In another embodiment, the composition comprises phenolic antimicrobial compounds and mixtures thereof. Antimicrobial components may be present from about 0.001% to about 20% by weight of the oral care composition. In another embodiment the antimicrobial agents generally comprise from about 0.1% to about 5% by weight of the oral care compositions of the present invention.

Other antimicrobial agents may be, but are not limited to, essential oils. Essential oils are volatile aromatic oils which may be synthetic or may be derived from plants by distillation, expression or extraction, and which usually carry the odor or flavor of the plant from which they are obtained. Useful essential oils may provide antiseptic activity. Some of these essential oils also act as flavoring agents. Useful essential oils include but are not limited to citra, thymol, menthol, methyl salicylate (wintergreen oil), eucalyptol, carvacrol, camphor, anethole, carvone, eugenol, isoeugenol, limonene, osimen, n-decyl alcohol, citronel, a-salpineol, methyl acetate, citronellyl acetate, methyl eugenol, cineol, linalool, ethyl linalaol, safrola vanillin, spearmint oil, peppermint oil, lemon oil, orange oil, sage oil, rosemary oil, cinnamon oil, pimento oil, laurel oil, cedar leaf oil, gerianol, verbenone, anise oil, bay oil, benzaldehyde, bergamot oil, bitter almond, chlorothymol, cinnamic aldehyde, citronella oil, clove oil, coal tar, eucalyptus oil, guaiacol, tropolone derivatives such as hinokitiol, avender oil, mustard oil, phenol, phenyl salicylate, pine oil, pine needle oil, sassafras oil, spike lavender oil, storax, thyme oil, tolu balsam, terpentine oil, clove oil, and combinations thereof. In one embodiment the essential oils are selected from thymol, methyl salicylate, eucalyptol, menthol and combinations thereof.

In one embodiment of the present invention, oral care compositions are provided comprising a blend of naturally occurring flavor ingredients or essential oils (EO) containing such flavor ingredients, the blend exhibiting excellent antimicrobial activity and comprising at least two components, a first component selected from acyclic or non-ring structures such as citral, neral, geranial, geraniol and nerol and a second component selected from ring-containing or cyclic structures such as eucalyptol, eugenol and carvacrol. Essential oils may be used to provide the above flavor ingredients including oils of lemongrass, citrus (orange, lemon, lime), citronella, geranium, rose, eucalyptus, oregano, bay and clove. However, it may be preferable that the flavor ingredients are provided as individual or purified chemicals rather than supplied in the composition by addition of natural oils or extracts as these sources may contain other components that may be unstable with other components of the composition or may introduce flavor notes that are incompatible with the desired flavor profile resulting in a less acceptable product from an organoleptic standpoint. Highly preferred for use herein are natural oils or extracts that have been purified or concentrated to contain mainly the desired component(s).

Preferably, the blend comprises 3, 4, 5 or more of the above components. Greater synergy in terms of antimicrobial efficacy may be obtained the more different components are blended together as long as the blend comprises at least one non-ring structure and one ring structure. A preferred blend comprises at least two ring structures or at least two non-ring structures. For example a blend comprising two non-ring structures (neral and geranial from citral) and eugenol as the ring structure is highly preferred for its efficacy against oral bacteria. Another preferred blend comprises three non-ring structures (geraniol, neral and geranial) and two ring structures (eugenol and eucalyptol). Examples of such blend is discussed in further detail in US published application 2008/0253976A1.

Other antibacterial agents may be basic amino acids and salts. Other embodiments may comprise arginine.

Anti-Plaque Agent

The dentifrice compositions of the present invention may include an anti-plaque agent such as stannous salts, copper salts, strontium salts, magnesium salts, copolymers of carboxylated polymers such as Gantrez or a dimethicone copolyol. The dimethicone copolyol is selected from C12 to C20 alkyl dimethicone copolyols and mixtures thereof. In one embodiment the dimethicone copolyol is cetyl dimethicone copolyol marketed under the Trade Name Abil EM90. The dimethicone copolyol in one embodiment can be present in a level of from about 0.001% to about 25%, in another embodiment from about 0.01% to about 5%, and in another embodiment from about 0.1% to about 1.5% by weight of the oral care composition.

Anti-Inflammatory Agent

Anti-inflammatory agents can also be present in the dentifrice compositions of the present invention. Such agents may include, but are not limited to, non-steroidal anti-inflammatory (NSAID) agents oxicams, salicylates, propionic acids, acetic acids and fenamates. Such NSAIDs include but are not limited to ketorolac, flurbiprofen, ibuprofen, naproxen, indomethacin, diclofenac, etodolac, indomethacin, sulindac, tolmetin, ketoprofen, fenoprofen, piroxicam, nabumetone, aspirin, diflunisal, meclofenamate, mefenamic acid, oxyphenbutazone, phenylbutazone and acetaminophen. Use of NSAIDs such as ketorolac are claimed in U.S. Pat. No. 5,626,838. Disclosed therein are methods of preventing and/or treating primary and reoccurring squamous cell carcinoma of the oral cavity or oropharynx by topical administration to the oral cavity or oropharynx of an effective amount of an NSAID. Suitable steroidal anti-inflammatory agents include corticosteroids, such as fluccinolone, and hydrocortisone.

Nutrients

Nutrients may improve the condition of the oral cavity and can be included in the dentifrice compositions of the present invention. Nutrients include minerals, vitamins, oral nutritional supplements, enteral nutritional supplements, and mixtures thereof. Useful minerals include calcium, phosphorus, zinc, manganese, potassium and mixtures thereof. Vitamins can be included with minerals or used independently. Suitable vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Oral nutritional supplements include amino acids, lipotropics, fish oil, and mixtures thereof. Amino acids include, but are not limited to L-Tryptophan, L-Lysine, Methionine, Threonine, Levocarnitine or L-carnitine and mixtures thereof. Lipotropics include, but are not limited to, choline, inositol, betaine, linoleic acid, linolenic acid, and mixtures thereof. Fish oil contains large amounts of Omega-3 (N-3) polyunsaturated fatty acids, eicosapentaenoic acid and docosahexaenoic acid. Enteral nutritional supplements include, but are not limited to, protein products, glucose polymers, corn oil, safflower oil, medium chain triglycerides. Minerals, vitamins, oral nutritional supplements and enteral nutritional supplements are described in more detail in Drug Facts and Comparisons (loose leaf drug information service), Wolters Kluer Company, St. Louis, Mo., ©1997, pps. 3-17 and 54-57.

Antioxidants

Antioxidants are generally recognized as useful in dentifrice compositions. Antioxidants are disclosed in texts such as Cadenas and Packer, The Handbook of Antioxidants, © 1996 by Marcel Dekker, Inc. Antioxidants useful in the present invention include, but are not limited to, Vitamin E, ascorbic acid, Uric acid, carotenoids, Vitamin A, flavonoids and polyphenols, herbal antioxidants, melatonin, aminoindoles, lipoic acids and mixtures thereof.

Analgesic and Anesthetic Agents

Anti-pain or desensitizing agents can also be present in the dentifrice compositions of the present invention. Analgesics are agents that relieve pain by acting centrally to elevate pain threshold without disturbing consciousness or altering other sensory modalities. Such agents may include, but are not limited to: strontium chloride; potassium nitrate; sodium fluoride; sodium nitrate; acetanilide; phenacetin; acertophan; thiorphan; spiradoline; aspirin; codeine; thebaine; levorphenol; hydromorphone; oxymorphone; phenazocine; fentanyl; buprenorphine; butaphanol; nalbuphine; pentazocine; natural herbs, such as gall nut; *Asarum*; Cubebin; Galanga; *scutellaria*; Liangmianzhen; and Baizhi. Anesthetic agents, or topical analgesics, such as acetaminophen, sodium salicylate, trolamine salicylate, lidocaine and benzocaine may also be present. These analgesic actives are described in detail in *Kirk-Othmer, Encyclopedia of Chemical Technology*, Fourth Edition, Volume 2, Wiley-Interscience Publishers (1992), pp. 729-737.

H-1 and H-2 Antagonists and Antiviral Actives

The present invention may also optionally comprise selective H-1 and H-2 antagonists including compounds disclosed in U.S. Pat. No. 5,294,433. Antiviral actives useful in the present composition include any know actives that are routinely use to treat viral infections. Such anti-viral actives are disclosed in *Drug Facts and Comparisons*, Wolters Kluer Company, ©1997, pp. 402(a)-407(z). Specific examples include anti-viral actives disclosed in U.S. Pat. No. 5,747,070, issued May 5, 1998. Said patent discloses the use of stannous salts to control viruses. Stannous salts and other anti-viral actives are described in detail in Kirk & Othmer, *Encyclopedia of Chemical Technology*, Third Edition, Volume 23, Wiley-Interscience Publishers (1982), pp. 42-71. The stannous salts that may be used in the present invention would include organic stannous carboxylates and inorganic stannous halides. While stannous fluoride may be used, it is typically used only in combination with another stannous halide or one or more stannous carboxylates or another therapeutic agent.

Chelating Agent

The present compositions may optionally contain chelating agents, also called chelants or sequestrants, many of which also have anticalculus activity or tooth substantive activity. Use of chelating agents in oral care products is advantageous for their ability to complex calcium such as found in the cell walls of bacteria. Chelating agents can also disrupt plaque by removing calcium from the calcium bridges which help hold this biomass intact. Chelating agents also have the ability to complex with metallic ions and thus aid in preventing their adverse effects on the stability or appearance of products. Chelation of ions, such as iron or copper, helps retard oxidative deterioration of finished products.

In addition, chelants can in principle remove stains by binding to teeth surfaces thereby displacing color bodies or chromagens. The retention of these chelants can also prevent stains from accruing due to disruption of binding sites of color bodies on tooth surfaces.

Therefore, chelants can aid in helping to mitigate stain and improve cleaning. A chelant may help to improve the cleaning as fused silica and abrasives clean in a mechanical mechanism while the chelant may help to provide chemical cleaning. Because the fused silica is a good mechanical cleaner, there may be more stain removed so a chelant may be desired to hold, suspend, or complex with the stain so it is not able to restain the tooth surface. Additionally, the chelant may coat the surface of the tooth to help prevent new stain.

Chelants may be desired to be added to formulations containing cationic antibacterial agents. It may be desired to add chelants to stannous containing formulations. The chelant is able to help stabilize the stannous and keep a higher amount of the stannous bioavailable. The chelant may be used in stannous formulations which have a pH above about 4.0. In some formulations, the stannous may be stable without the need for a chelant as the stannous is more stable with fused silica as compared to precipitated silica.

Suitable chelating agents include soluble phosphate compounds, such as phytates and linear polyphosphates having two or more phosphate groups, including tripolyphosphate, tetrapolyphosphate and hexametaphosphate, among others. Preferred polyphosphates are those having the number of phosphate groups n averaging from about 6 to about 21, such as those commercially known as Sodaphos (n≈6), Hexaphos (n≈13), and Glass H (n≈21). Other polyphosphorylated compounds may be used in addition to or instead of the polyphosphate, in particular polyphosphorylated inositol compounds such as phytic acid, myo-inositol pentakis(dihydrogen phosphate); myo-inositol tetrakis(dihydrogen phosphate), myo-inositol trikis(dihydrogen phosphate), and an alkali metal, alkaline earth metal or ammonium salt thereof. Preferred herein is phytic acid, also known as myo-inositol 1,2,3,4,5,6-hexakis (dihydrogen phosphate) or inositol hexaphosphoric acid, and its alkali metal, alkaline earth metal or ammonium salts. Herein, the term "phytate" includes phytic acid and its salts as well as the other polyphosphorylated inositol compounds. The amount of chelating agent in the compositions will depend on the chelating agent used and typically will be from at least about 0.1% to about 20%, preferably from about 0.5% to about 10% and more preferably from about 1.0% to about 7%.

Still other phosphate compounds that are useful herein for their ability to bind, solubilize and transport calcium are the surface active organophosphate compounds described above useful as tooth substantive agents including organic phosphate mono-, di- or triesters.

Other suitable agents with chelating properties for use in controlling plaque, calculus and stain include polyphosphonates described in U.S. Pat. No. 3,678,154 to Widder et al., U.S. Pat. No. 5,338,537 to White, Jr., and U.S. Pat. No. 5,451, to Zerby et al.; carbonyl diphosphonates in U.S. Pat. No. 3,737,533 to Francis; acrylic acid polymer or copolymer in U.S. Pat. No. 4,847,070, Jul. 11, 1989 to Pyrz et al. and in U.S. Pat. No. 4,661,341, Apr. 28, 1987 to Benedict et al.; sodium alginate in U.S. Pat. No. 4,775,525, issued Oct. 4, 1988, to Pera; polyvinyl pyrrolidone in GB 741,315, WO 99/12517 and U.S. Pat. No. 5,538,714 to Pink et al.; and copolymers of vinyl pyrrolidone with carboxylates in U.S. Pat. No. 5,670,138 to Venema et al. and in JP Publication No. 2000-0633250 to Lion Corporation.

Still other chelating agents suitable for use in the present invention are the anionic polymeric polycarboxylates. Such materials are well known in the art, being employed in the form of their free acids or partially or preferably fully neutralized water soluble alkali metal (e.g. potassium and preferably sodium) or ammonium salts. Examples are 1:4 to 4:1 copolymers of maleic anhydride or acid with another polymerizable ethylenically unsaturated monomer, preferably methyl vinyl ether (methoxyethylene) having a molecular weight (M.W.) of about 30,000 to about 1,000,000. These copolymers are available for example as Gantrez® AN 139 (M.W. 500,000), AN 119 (M.W. 250,000) and S-97 Pharmaceutical Grade (M.W. 70,000), of GAF Chemicals Corporation.

Other operative polymeric polycarboxylates include the 1:1 copolymers of maleic anhydride with ethyl acrylate, hydroxyethyl methacrylate, N-vinyl-2-pyrrolidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Additional operative polymeric polycarboxylates are disclosed in U.S. Pat. No. 4,138,477, Feb. 6, 1979 to Gaffar and U.S. Pat. No. 4,183,914, Jan. 15, 1980 to Gaffar et al. and include copolymers of maleic anhydride with styrene, isobutylene or ethyl vinyl ether; polyacrylic, polyitaconic and polymaleic acids; and sulfoacrylic oligomers of M.W. as low as 1,000 available as Uniroyal ND-2.

Other suitable chelants include polycarboxylic acids and salts thereof described in U.S. Pat. Nos. 5,015,467 to Smitherman 5,849,271 and 5,622,689 both to Lukacovic; such as tartaric acid, citric acid, gluconic acid, malic acid; succinic acid, disuccinic acid and salts thereof, such as sodium or potassium gluconate and citrate; citric acid/alkali metal citrate combination; disodium tartrate; dipotassium tartrate; sodium potassium tartrate; sodium hydrogen tartrate; potassium hydrogen tartrate; acid or salt form of sodium tartrate monosuccinate, potassium tartrate disuccinate, and mixtures thereof. In some embodiments, there may be mixtures or combinations of chelating agents.

Tooth Substantive Agent

The present invention may include a tooth substantive agent. For purposes of this application, tooth substantive agents are included as chelants also. Suitable agents may be polymeric surface active agents (PMSA's), including polyelectrolytes, more specifically anionic polymers. The PMSA's contain anionic groups, e.g., phosphate, phosphonate, carboxy, or mixtures thereof, and thus, have the capability to interact with cationic or positively charged entities. The "mineral" descriptor is intended to convey that the surface activity or substantivity of the polymer is toward mineral surfaces such as calcium phosphate minerals in teeth.

PMSA's are useful in the present compositions because of their many benefits such as stain prevention. It is believed the PMSA's provide a stain prevention benefit because of their reactivity or substantivity to mineral or tooth surfaces, resulting in desorption of portions of undesirable adsorbed pellicle proteins, in particular those associated with binding color bodies that stain teeth, calculus development and attraction of undesirable microbial species. The retention of these PMSA's on teeth can also prevent stains from accruing due to disruption of binding sites of color bodies on tooth surfaces.

The ability of PMSA's to bind stain promoting ingredients of oral care products such as stannous ions and cationic antimicrobials is also believed to be helpful. The PMSA will also provide tooth surface conditioning effects which produce desirable effects on surface thermodynamic properties and surface film properties, which impart improved clean feel aesthetics both during and most importantly, following rinsing or brushing. Many of these agents are also expected to provide tartar control benefits when included in oral compositions, hence providing improvement in both the appearance of teeth and their tactile impression to consumers.

The PMSA's include any agent which will have a strong affinity for the tooth surface, deposit a polymer layer or coating on the tooth surface and produce the desired surface modification effects. Suitable examples of such polymers are polyelectrolytes such as condensed phosphorylated polymers; polyphosphonates; copolymers of phosphate- or phosphonate-containing monomers or polymers with other monomers such as ethylenically unsaturated monomers and amino acids or with other polymers such as proteins, polypeptides, polysaccharides, poly(acrylate), poly(acrylamide), poly (methacrylate), poly(ethacrylate), poly(hydroxyalkylmethacrylate), poly(vinyl alcohol), poly(maleic anhydride), poly(maleate) poly(amide), poly(ethylene amine), poly(ethylene glycol), poly(propylene glycol), poly(vinyl acetate) and poly(vinyl benzyl chloride); polycarboxylates and carboxy-substituted polymers; and mixtures thereof. Suitable polymeric mineral surface active agents include the carboxy-substituted alcohol polymers described in U.S. Pat. Nos. 5,292,501; 5,213,789, 5,093,170; 5,009,882; and 4,939,284; all to Degenhardt et al. and the diphosphonate-derivatized polymers in U.S. Pat. No. 5,011,913 to Benedict et al; the synthetic anionic polymers including polyacrylates and copolymers of maleic anhydride or acid and methyl vinyl ether (e.g., Gantrez®), as described, for example, in U.S. Pat. No. 4,627,977, to Gaffar et al. A preferred polymer is diphosphonate modified polyacrylic acid. Polymers with activity must have sufficient surface binding propensity to desorb pellicle proteins and remain affixed to enamel surfaces. For tooth surfaces, polymers with end or side chain phosphate or phosphonate functions are preferred although other polymers with mineral binding activity may prove effective depending upon adsorption affinity.

Additional examples of suitable phosphonate containing polymeric mineral surface active agents include the geminal diphosphonate polymers disclosed as anticalculus agents in U.S. Pat. No. 4,877,603 to Degenhardt et al; phosphonate group containing copolymers disclosed in U.S. Pat. No. 4,749,758 to Dursch et al. and in GB 1,290,724 (both assigned to Hoechst) suitable for use in detergent and cleaning compositions; and the copolymers and cotelomers disclosed as useful for applications including scale and corrosion inhibition, coatings, cements and ion-exchange resins in U.S. Pat. No. 5,980,776 to Zakikhani et al. and U.S. Pat. No. 6,071,434 to Davis et al. Additional polymers include the water-soluble copolymers of vinylphosphonic acid and acrylic acid and salts thereof disclosed in GB 1,290,724 wherein the copolymers contain from about 10% to about 90% by weight vinylphosphonic acid and from about 90% to about 10% by weight acrylic acid, more particularly wherein the copolymers have a weight ratio of vinylphosphonic acid to acrylic acid of 70% vinylphosphonic acid to 30% acrylic acid; 50% vinylphosphonic acid to 50% acrylic acid; or 30% vinylphosphonic acid to 70% acrylic acid. Other suitable polymers include the water soluble polymers disclosed by Zakikhani and Davis prepared by copolymerizing diphosphonate or polyphosphonate monomers having one or more unsaturated C=C bonds (e.g., vinylidene-1,1-diphosphonic acid and 2-(hydroxyphosphinyl)ethylidene-1,1-diphosphonic acid), with at least one further compound having unsaturated C=C bonds (e.g., acrylate and methacrylate monomers). Suitable polymers include the diphosphonate/acrylate polymers supplied by Rhodia under the designation ITC 1087 (Average MW 3000-60,000) and Polymer 1154 (Average MW 6000-55,000).

A preferred PMSA will be stable with other components of the oral care composition such as ionic fluoride and metal ions. Also preferred are polymers that have limited hydrolysis in high water content formulations, thus permitting a simple single phase dentifrice or mouthrinse formulation. If the PMSA does not have these stability properties, one option is a dual phase formulation with the polymeric mineral surface active agent separated from the fluoride or other incompatible component. Another option is to formulate non-aqueous, essentially non-aqueous or limited water compositions to minimize reaction between the PMSA and other components.

One preferred PMSA is a polyphosphate. A polyphosphate is generally understood to consist of two or more phosphate molecules arranged primarily in a linear configuration, although some cyclic derivatives may be present. Although pyrophosphates (n=2) are technically polyphosphates, the polyphosphates desired are those having around three or more phosphate groups so that surface adsorption at effective concentrations produces sufficient non-bound phosphate functions, which enhance the anionic surface charge as well as hydrophilic character of the surfaces. The inorganic polyphosphate salts desired include tripolyphosphate, tetrapolyphosphate and hexametaphosphate, among others. Polyphosphates larger than tetrapolyphosphate usually occur as amorphous glassy materials. Preferred in the present compositions are the linear polyphosphates having the formula:

$$XO(XPO_3)_nX$$

wherein X is sodium, potassium or ammonium and n averages from about 3 to about 125. Preferred polyphosphates are those having n averaging from about 6 to about 21, such as those commercially known as Sodaphos (n≈6), Hexaphos (n≈13), and Glass H (n≈21) and manufactured by FMC Corporation and Astaris. These polyphosphates may be used alone or in combination. Polyphosphates are susceptible to hydrolysis in high water formulations at acid pH, particularly below pH 5. Thus it is preferred to use longer-chain polyphosphates, in particular Glass H with an average chain length of about 21. It is believed such longer-chain polyphosphates when undergoing hydrolysis produce shorter-chain polyphosphates which are still effective to deposit onto teeth and provide a stain preventive benefit.

Also useful as tooth substantive agents are nonpolymeric phosphate compounds, in particular polyphosphorylated inositol compounds such as phytic acid, myo-inositol pentakis(dihydrogen phosphate); myo-inositol tetrakis(dihydrogen phosphate), myo-inositol trikis(dihydrogen phosphate), and an alkali metal, alkaline earth metal or ammonium salt thereof. Preferred herein is phytic acid, also known as myo-inositol 1,2,3,4,5,6-hexakis (dihydrogen phosphate) or inositol hexaphosphoric acid, and its alkali metal, alkaline earth metal or ammonium salts. Herein, the term "phytate" includes phytic acid and its salts as well as the other polyphosphorylated inositol compounds.

Other surface active phosphate compounds useful as tooth substantive agents include organophosphates such as phosphate mono-, di- or triesters such as described in commonly assigned application published as US20080247973A1. Examples include mono- di- and tri-alkyl and alkyl (poly) alkoxy phosphates such as dodecyl phosphate, lauryl phosphate; laureth-1 phosphate; laureth-3 phosphate; laureth-9 phosphate; dilaureth-10 phosphate; trilaureth-4 phosphate; C12-18 PEG-9 phosphate and salts thereof. Many are commercially available from suppliers including Croda; Rhodia; Nikkol Chemical; Sunjin; Alzo; Huntsman Chemical; Clariant and Cognis. Some preferred agents are polymeric, for example those containing repeating alkoxy groups as the polymeric portion, in particular 3 or more ethoxy, propoxy isopropoxy or butoxy groups.

Additional suitable polymeric organophosphate agents include dextran phosphate, polyglucoside phosphate, alkyl polyglucoside phosphate, polyglyceryl phosphate, alkyl polyglyceryl phosphate, polyether phosphates and alkoxylated polyol phosphates. Some specific examples are PEG phosphate, PPG phosphate, alkyl PPG phosphate, PEG/PPG phosphate, alkyl PEG/PPG phosphate, PEG/PPG/PEG phosphate, dipropylene glycol phosphate, PEG glyceryl phosphate, PBG (polybutylene glycol) phosphate, PEG cyclodextrin phosphate, PEG sorbitan phosphate, PEG alkyl sorbitan phosphate, and PEG methyl glucoside phosphate.

Additional suitable non-polymeric phosphates include alkyl mono glyceride phosphate, alkyl sorbitan phosphate, alkyl methyl glucoside phosphate, alkyl sucrose phosphates.

Other useful tooth substantive agents include siloxane polymers functionalized with carboxylic acid groups, such as disclosed in disclosed in U.S. Pat. Nos. 7,025,950 and 7,166,235 both assigned to The Procter & Gamble Co. These polymers comprise a hydrophobic siloxane backbone and pendant anionic moieties containing carboxy groups and have the ability to deposit onto surfaces from aqueous-based formulations or from essentially non-aqueous based formulations, forming a substantially hydrophobic coating on the treated surface. The carboxy functionalized siloxane polymers are believed to attach themselves to polar surfaces and to form a coating thereon by electrostatic interaction, i.e., complex formation between the pendant carboxy groups with calcium ions present in teeth. The carboxy groups thus serve to anchor the siloxane polymer backbone onto a surface thereby modifying it to be hydrophobic, which then imparts a variety of end use benefits to that surface such as ease of cleaning, stain removal and prevention, whitening, etc. The carboxy functionalized siloxane polymer further acts to enhance deposition of active agents onto the surface and to improve retention and efficacy of these actives on the treated surface.

Also useful as tooth substantive agents are water-soluble or water-dispersible polymeric agents prepared by copolymerizing one or a mixture of vinyl pyrrolidone (VP) monomers with one or a mixture of alkenyl carboxylate (AC) monomers, specifically C2-C12 alkenyl esters of saturated straight- or branched-chain C1-C19 alkyl carboxylic acids described in commonly assigned U.S. Pat. No. 6,682,722. Examples include copolymers of vinyl pyrrolidone with one or a mixture of vinyl acetate, vinyl propionate, or vinyl butyrate. Preferred polymers have an average molecular weight ranging from about 1,000 to about 1,000,000, preferably from 10,000 to 200,000, even more preferably from 30,000 to 100,000.

The amount of tooth substantive agent will typically be from about 0.1% to about 35% by weight of the total oral composition. In dentifrice formulations, the amount is preferably from about 2% to about 30%, more preferably from about 5% to about 25%, and most preferably from about 6% to about 20%. In mouthrinse compositions, the amount of tooth substantive agent is preferably from about 0.1% to 5% and more preferably from about 0.5% to about 3%.

Additional Actives

Additional actives suitable for use in the present invention may include, but are not limited to, insulin, steroids, herbal and other plant derived remedies. Additionally, anti-gingivitis or gum care agents known in the art may also be included. Components which impart a clean feel to the teeth may optionally be included. These components may include, for example, baking soda or Glass-H. Also, it is recognized that in certain forms of therapy, combinations of these above-named agents may be useful in order to obtain an optimal effect. Thus, for example, an anti-microbial and an anti-inflammatory agent may be combined in a single dentifrice composition to provide combined effectiveness.

Optional agents to be used include such known materials as synthetic anionic polymers, including polyacrylates and copolymers of maleic anhydride or acid and methyl vinyl ether (e.g., Gantrez), as described, for example, in U.S. Pat. No. 4,627,977, as well as, e.g., polyamino propoane sulfonic acid (AMPS), zinc citrate trihydrate, polyphosphates (e.g., tripolyphosphate; hexametaphosphate), diphosphonates (e.g., EHDP; AHP), polypeptides (such as polyaspartic and polyglutamic acids), and mixtures thereof. Additionally, the dentifrice composition can include a polymer carrier, such as those described in U.S. Pat. Nos. 6,682,722 and 6,589,512 and U.S. application Ser. Nos. 10/424,640 and 10/430,617.

Other Optional Ingredients

Buffering Agents

The dentifrice compositions may contain a buffering agent. Buffering agents, as used herein, refer to agents that can be used to adjust the pH of the dentifrice compositions to a range of about pH 3.0 to about pH 10. The buffering agents include alkali metal hydroxides, ammonium hydroxide, organic ammonium compounds, carbonates, sesquicarbonates, borates, silicates, phosphates, imidazole, and mixtures thereof. Specific buffering agents include monosodium phosphate, trisodium phosphate, sodium benzoate, benzoic acid, sodium hydroxide, potassium hydroxide, alkali metal carbonate salts, sodium carbonate, imidazole, pyrophosphate salts, sodium gluconate, lactic acid, sodium lactate, citric acid, and sodium citrate. Buffering agents are used at a level of from about 0.1% to about 30%, preferably from about 0.1% to about 10%, and more preferably from about 0.3% to about 3%, by weight of the dentifrice compositions.

Coloring Agent

Coloring agents may also be added to the present composition. The coloring agent may be in the form of an aqueous solution, preferably 1% coloring agent in a solution of water. Pigments, pealing agents, filler powders, talc, mica, magnesium carbonate, calcium carbonate, bismuth oxychloride, zinc oxide, and other materials capable of creating a visual change to the dentifrice compositions may also be used. Color solutions and other agents generally comprise from about 0.01% to about 5%, by weight of the composition. Titanium dioxide may also be added to the present composition. Titanium dioxide is a white powder which adds opacity to the compositions. Titanium dioxide generally comprises from about 0.25% to about 5%, by weight of the composition.

Flavoring Agent

Suitable flavoring components include oil of wintergreen, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, cranberry, chocolate, green tea, and mixtures thereof. The essential oils may also be included as flavoring agents and are described above in the discussion of antibacterial agents. Coolants may also be part of the flavor composition. Coolants suitable for the present compositions include the paramenthan carboxyamide agents such as N-ethyl-p-menthan-3-carboxamide (known commercially as WS-3, WS-23, WS-5), MGA, TK-10, Physcool, and mixtures thereof. Salivating agents, warming agents, numbing agents, and other optional materials can be used to deliver a signal while the oral composition is being used. Due to the interactivity of precipitated silicas, flavor components may become trapped or emulsified, in effect disappearing so as to not be perceived by a user. In contrast, fused silica's lack of interactivity may impact the amount of a flavor component that must be added to achieve a noticeable effect. In some embodiments, the amount of flavoring agent present, by weight of the composition, may be about 10%, about 20%, or about 50% less than comparable precipitated silica formulations while achieving the same flavor impact.

A flavor composition is generally used in the oral care compositions at levels of from about 0.001% to about 5%, by weight of the oral care composition. The flavor composition will preferably be present in an amount of from about 0.01% to about 4%, more preferably from about 0.1% to about 3%, and more preferably from about 0.5% to about 2% by weight.

Similarly, coolants may not be absorbed as much in the present compositions, meaning that the coolants may last longer, or may be used in lesser amounts. Essential oils also may be absorbed less so that less may be used to achieve the same effectiveness. The fused silica may not attach to the taste receptor like precipitated silica does, meaning that the taste receptor may be more accessible to the flavoring agent.

Other aesthetic benefits may be apparent to users, such as a clean mouth experience and an increased perception of sweetness or coolness, for example. The improved slick, clean mouthfeel may contribute to a lesser perception of dry mouth, and well as the improved cleaning of the fused silica may help remove layers of muscin and increase the perception of moisturization. Another consumer aesthetic benefit may be improved rinsing out of the mouth of the oral composition, due to the inert fused silica particles not clumping, but remaining dispersed while the user brushes. Yet another potential benefit is improved foaming Again, because the fused silica is less reactive than precipitated silica, surfactants are more available and improved foaming may result.

Some embodiments may comprise a TRPV1 activator, a transient receptor potential vanilloid receptor 1 activator, which is a ligand-gated, non-selective cation channel preferentially expressed on small-diameter sensory neurons and detects noxious as well as other substances. By adding a TRPV1 activator to an oral care composition with an off tasting component, the user of the composition may experience an improved taste over an oral care composition without the TRPV1 activator. Thus, the TRPV1 activator works to off-set the bad taste associated with many components used in oral care compositions. These activators may not only off-set bad tastes, but may also reduce dryness perception, by limiting the mouth's ability to perceive dryness. In one embodiment, the TRPV1 activator comprises vanillyl butyl ether, zingerone, capsaicin, capsiate, shoagol, gingerol, piperine, or a combination thereof. In one embodiment, a TRPV1 activator will be added in an amount of about 0.0001% to about 0.25% by weight of the oral care composition.

Sweetener

Sweetening agents can be added to the compositions. These include sweeteners such as saccharin, dextrose, sucrose, lactose, xylitol, maltose, levulose, aspartame, sodium cyclamate, D-tryptophan, dihydrochalcones, acesulfame, sucralose, neotame, and mixtures thereof. Various coloring agents may also be incorporated in the present invention. Sweetening agents are generally used in oral compositions at levels of from about 0.005% to about 5%, by weight of the composition.

Thickening Agents

Additional thickening agents, such as polymeric thickeners, may be utilized. Suitable thickening agents are carboxyvinyl polymers, carrageenan, hydroxyethyl cellulose, laponite and water soluble salts of cellulose ethers such as sodium carboxymethylcellulose and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture. Other thickeners may include alkylated polyacrylates, alkylated cross-linked polyacrylates, or gel networks. Thickening agents can include polymeric polyether compounds, e.g., polyethylene or polypropylene oxide (M.W. 300 to 1,000,000), capped with alkyl or acyl groups containing 1 to about 18 carbon atoms.

A suitable class of thickening or gelling agents includes a class of homopolymers of acrylic acid crosslinked with an alkyl ether of pentaerythritol or an alkyl ether of sucrose, or carbomers. Carbomers are commercially available from B.F. Goodrich as the Carbopol® series. Particularly the carbopols include Carbopol 934, 940, 941, 956, and mixtures thereof.

Copolymers of lactide and glycolide monomers, the copolymer having the molecular weight in the range of from about 1,000 to about 120,000 (number average), are useful for delivery of actives into the periodontal pockets or around the periodontal pockets as a "subgingival gel carrier." These polymers are described in U.S. Pat. Nos. 5,198,220; 5,242,910; and 4,443,430.

Due to precipitated silica's interaction with other formulation components, precipitated silica can affect the rheology of a composition over time. Fused silica, however, due to its lack of interaction with other formulation components, has little impact on rheology. This means that oral care compositions formulated with fused silica are more stable over time, which, among other things, can allow for better cleaning and better predictability. Thus, in some embodiments, thickening agents, combinations and amounts, may be very different from those of traditional dentifrices. In the present invention, thickening agents may be used in an amount from about 0% to about 15%, or from about 0.01% to about 10%, or in another embodiment from about 0.1% to about 5%, by weight of the total oral composition.

In some embodiments of the present invention, the composition may comprise a thickening agent selected from natural and synthetic sources. In some embodiments, the thickening agent may be selected from the group consisting of clay, laponite, and mixtures thereof. In some embodiments, the composition may further comprise a thickening agent selected from the group consisting of carboxyvinyl polymers, carrageenan, hydroxyethyl cellulose, water soluble salts of cellulose ethers such as sodium carboxymethylcellulose, cross-linked carboxymethylcellulose, sodium hydroxyethyl cellulose, cross-linked starch, natural gums such as gum karaya, xanthan gum, gum arabic, and gum tragacanth, magnesium aluminum silicate, silica, alkylated polyacrylates, alkylated cross linked polyacrylates, and mixtures thereof.

Other possible thickeners include carbomers, hydrophobically modified carbomers, carboxymethyl cellulose, cetyl/stearyl alcohol, sodium alginate, gellan gum, acylated gellan gum, sodium hydroxypropyl starch phosphate, microcrystalline cellulose, micro fibrous cellulose, crosslinked polyvinyl pyrrolidone, cetyl hydroxyethyl cellulose, crosslinked sodium acryloyl methyl propane sulfonic acid and copolymers, and mixtures thereof.

The viscosity of the composition at the time it is made may remain the viscosity of the composition, or, stated differently, the composition may have a stable viscosity. For the viscosity to be considered stable, typically the viscosity changes no more than about 5% after 30 days. In some embodiments, the viscosity of the composition does not change by more than about 5% after about 30 days, by more than about 10% after about 30 days, by more than about 20% after about 30 days, or by more than about 50% after about 90 days. Because the problem of unstable viscosity over time is more pronounced in formulations with low water amounts, in some embodiments, the compositions of the present invention may contain less than about 20% total water, or less than about 10% total water.

Gel Networks

A gel network can be used in the oral composition. The gel network can be used to structure the oral composition or to aid in delivering an active, flavor, or other reactive material. The gel network may be used to structure, meaning to thicken or provide the desired rheology, for the fused silica oral compositions by itself or in combination with another thickener or structuring agent. A gel network composition has a rheology that may be advantageous for fused silica as fused silica is more dense than some other abrasives or materials in the oral composition. Because the fused silica is heavier or more dense, it may fall or drop out of the composition or solution more easily than other less dense materials. This may be when the composition is diluted with water. For example, when a dentifrice is used for brushing, it is diluted by water when in the mouth. The dilution rheology for a dentifrice containing a gel network aiding in structuring the dentifrice may be higher than dentifrices structured with polymeric or more typical thickening materials. A higher dilution rheology is beneficial in keeping the fused silica suspended and allowing the fused silica to participate more fully in the cleaning process. If a material, such as the abrasive, is not suspended or maintained in the composition once diluted, the cleaning efficacy, such as pellicle cleaning ratio, may decrease. Additionally, as more of the abrasive or fused silica is suspended, the oral composition may contain less abrasives overall since more of the abrasive is able to participate in the cleaning. FIG. 13 shows PCR and RDA data for compositions structured by gel networks compared to compositions which are not structured by gel networks but thickened with typical polymeric binders. As shown, the PCR score increases from 92.5 to 127.56 and from 95.44 to 121.04 when a gel network is used in a formula containing 15% fused silica. This PCR increase of greater than about 10%, about 15%, about 20%, or about 25% may be due to the gel networks ability to suspend more of the fused silica during cleaning. While the cleaning scores increase, the abrasion remains in acceptable ranges.

The oral compositions of the present invention may comprise a dispersed gel network. As used herein, the term "gel network" refers to a lamellar or vesicular solid crystalline phase which comprises at least one fatty amphiphile, at least one surfactant, and a solvent. The lamellar or vesicular phase comprises bi-layers made up of a first layer comprising the fatty amphiphile and the secondary surfactant and alternating with a second layer comprising the solvent. For the lamellar crystalline phase to form, the fatty amphiphile and secondary surfactant must be dispersed within the solvent. The term "solid crystalline", as used herein, refers to the structure of the lamellar or vesicular phase which forms at a temperature below the chain melt temperature of the layer in the gel network comprising the one or more fatty amphiphiles. The gel networks suitable for use in the present invention are described in more detail in US 2008/0081023A1 which describes the materials, methods of making, and uses of the gel networks. Additionally, US 2009/0246151A1 also describes gel networks and method of making the compositions containing gel networks.

The gel network in the oral composition can be used to structure the oral composition. The structuring provided by the gel network provides the desired rheology or viscosity by thickening the oral composition. The structuring can be done without the need for polymeric thickening agents, however, polymeric thickeners or other agents could be used in addition to the gel network to structure the oral composition. Because the fused silica does not provide any or as much thickening as a typical precipitated silica, the thickening of the oral composition may benefit more from a gel network used to structure the oral composition. The small or no effect that the fused silica has the viscosity or thickening of the oral composition also may provide the benefit of being able to formulate an oral composition with a gel network or other thickening system and then being able to add as much fused silica as desired without needing to readjust the level of thickening as would be required if the amount of precipitated silica was adjusted.

The gel network component of the present invention comprises at least one fatty amphiphile. As used herein, "fatty amphiphile" refers to a compound having a hydrophobic tail group and a hydrophilic head group which does not make the compound water soluble (immiscible), wherein the compound also has a net neutral charge at the pH of the oral composition. The fatty amphiphile can be selected from the group consisting of fatty alcohols, alkoxylated fatty alcohols, fatty phenols, alkoxylated fatty phenols, fatty amides, alkyoxylated fatty amides, fatty amines, fatty alkylamidoalkylamines, fatty alkyoxylated amines, fatty carbamates, fatty amine oxides, fatty acids, alkoxylated fatty acids, fatty diesters, fatty sorbitan esters, fatty sugar esters, methyl glucoside esters, fatty glycol esters, mono, di- and tri-glycerides, polyglycerine fatty esters, alkyl glyceryl ethers, propylene glycol fatty acid esters, cholesterol, ceramides, fatty silicone waxes, fatty glucose amides, phospholipids, and combinations thereof. Suitable fatty amphiphiles include a combination of cetyl alcohol and stearyl alcohol.

The gel network also comprises a surfactant. One or more surfactants are combined with the fatty amphiphile and oral carrier to form the gel network of the present invention. The surfactant is typically water soluble or miscible in the solvent or oral carrier. Suitable surfactants include anionic, zwitterionic, amphoteric, cationic, and nonionic surfactants. In one embodiment, anionic surfactants such as sodium lauryl sulfate, are preferred. The surfactants may be a combination of more than one type of surfactants, such as an anionic and nonionic surfactant. The gel network will likely also comprise solvents, such as water or other suitable solvents. The solvent and the surfactant together contribute to the swelling of the fatty amphiphile. This, in turn, leads to the formation and the stability of the gel network. In addition to forming the gel network, the solvent can help to keep the dentifrice composition from hardening upon exposure to air and provide a moist feel in the mouth. The solvent, as used herein, refers to suitable solvents which can be used in the place of or in combination with water in the formation of the gel network of the present invention. Suitable solvents for the present invention include water, edible polyhydric alcohols such as glycerin, diglycerin, triglycerin, sorbitol, xylitol, butylene glycol, erythritol, polyethylene glycol, propylene glycol, and combinations thereof. Sorbitol, glycerin, water, and combinations thereof are preferred solvents.

To form a gel network, the oral compositions may comprise fatty amphiphile in an amount from about 0.05% to about 30%, preferably from about 0.1% to about 20%, and more preferably from about 0.5% to about 10%, by weight of the oral composition. The amount of fatty amphiphile will be chosen based on the formation of the gel network and the composition of the oral formulation. For example, an oral composition containing low amounts of water may require about 1% of a fatty amphiphile whereas an oral composition with higher amounts of water may require 6% or more of a fatty amphiphile. The amount of surfactant and solvent needed to form the gel network will also vary based on the materials chosen, the function of the gel network, and amount of fatty amphiphile. The surfactant as part of gel network phase is typically in an amount from about 0.01% to about 15%, preferably from about 0.1% to about 10%, and more preferably from about 0.3% to about 5%, by weight of the oral composition. In some embodiments, a diluted solution of surfactant in water is utilized. In one embodiment, the amount of surfactant is chosen based on the level of foaming desired in the oral composition and on the irritation caused by the surfactant. The solvent may be present in an amount suitable to achieve a gel network when combined with fatty amphiphile and surfactant according to the present invention. The oral compositions may comprise at least about 0.05% of a solvent, by weight of the oral composition. The solvent may be present in the oral composition in amount of from about 0.1% to about 99%, from about 0.5% to about 95%, and from about 1% to about 90%.

Humectant

A humectant can help to keep the dentifrice composition from hardening upon exposure to air and provide a moist feel in the mouth. A humectant or additional solvent may be added to the oral carrier phase. Suitable humectants for the present invention include water, edible polyhydric alcohols such as glycerin, sorbitol, xylitol, butylene glycol, polyethylene glycol, propylene glycol, and combinations thereof. Sorbitol, glycerin, water, and combinations thereof are preferred humectants. The humectant may be present in an amount of from about 0.1% to about 99%, from about 0.5% to about 95%, and from about 1% to about 90%.

Surfactants

A surfactant may be added to the dentifrice composition. Surfactants, also commonly referred to as sudsing agents, may aid in the cleaning or foaming of the dentifrice composition. Suitable surfactants are those which are reasonably stable and foam throughout a wide pH range. The surfactant may be anionic, nonionic, amphoteric, zwitterionic, cationic, or mixtures thereof.

Examples of anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate (SLS) and sodium coconut monoglyceride sulfonates are examples of anionic surfactants of this type. Examples of other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed by Agricola et al., U.S. Pat. No. 3,959,458, issued May 25, 1976. In some embodiments, the oral care composition may comprise an anionic surfactant at a level of from about 0.025% to about 9%, from about 0.05% to about 5% in some embodiments, and from about 0.1% to about 1% in other embodiments.

Another suitable surfactant is one selected from the group consisting of sarcosinate surfactants, isethionate surfactants and taurate surfactants. Preferred for use herein are alkali metal or ammonium salts of these surfactants, such as the sodium and potassium salts of the following: lauroyl sarcosinate, myristoyl sarcosinate, palmitoyl sarcosinate, stearoyl sarcosinate and oleoyl sarcosinate. The sarcosinate surfactant may be present in the compositions of the present invention from about 0.1% to about 2.5%, or from about 0.5% to about 2% by weight of the total composition.

Cationic surfactants useful in the present invention include derivatives of aliphatic quaternary ammonium compounds having one long alkyl chain containing from about 8 to 18 carbon atoms such as lauryl trimethylammonium chloride; cetyl pyridinium chloride; cetyl trimethylammonium bromide; di-isobutylphenoxyethyl-dimethylbenzylammonium chloride; coconut alkyltrimethylammonium nitrite; cetyl pyridinium fluoride; etc. Preferred compounds are the quaternary ammonium fluorides described in U.S. Pat. No. 3,535,421, Oct. 20, 1970, to Briner et al., where said quaternary ammonium fluorides have detergent properties. Certain cationic surfactants can also act as germicides in the compositions disclosed herein.

Nonionic surfactants that can be used in the compositions of the present invention include compounds produced by the condensation of alkylene oxide groups (hydrophilic in nature) with an organic hydrophobic compound which may be aliphatic or alkylaromatic in nature. Examples of suitable nonionic surfactants include the Pluronics, polyethylene oxide condensates of alkyl phenols, products derived from the condensation of ethylene oxide with the reaction product of propylene oxide and ethylene diamine, ethylene oxide condensates of aliphatic alcohols, acids, and esters, long chain tertiary amine oxides, long chain tertiary phosphine oxides, long chain dialkyl sulfoxides and mixtures of such materials.

Zwitterionic synthetic surfactants useful in the present invention include derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate or phosphonate.

Suitable betaine surfactants are disclosed in U.S. Pat. No. 5,180,577 to Polefka et al., issued Jan. 19, 1993. Typical alkyl dimethyl betaines include decyl betaine or 2-(N-decyl-N,N-dimethylammonio) acetate, coco betaine or 2-(N-coc-N,N-dimethyl ammonio) acetate, myristyl betaine, palmityl betaine, lauryl betaine, cetyl betaine, cetyl betaine, stearyl betaine, etc. The amidobetaines are exemplified by cocoamidoethyl betaine, cocoamidopropyl betaine, lauramidopropyl betaine and the like. The betaines of choice are preferably the cocoamidopropyl betaine and, more preferably, the lauramidopropyl betaine.

Precipitated silica tends to lessen the foaming of an oral composition. In contrast, fused silica, with its low reactivity, does not inhibit foaming, or does not inhibit foaming to the degree of precipitated silica. The lack of interference with surfactant components can impact the amount of surfactant used, which in turn may affect other variables. For example, if less surfactant is needed to achieve acceptable consumer foaming, this may reduce irritancy (a known consumer negative of SLS), or could lower the composition pH, which could allow better fluoride uptake.

In some embodiments, polymeric mineral surface active agents are added to mitigate negative aesthetics of these compounds. The polymeric mineral surface active agents may be organo phosphate polymers, which in some embodiments are alkyl phosphate esters or salts thereof, ethoxylated alkyl phosphate esters and salts thereof, or mixtures of alkyl phosphate esters or salts thereof. In some embodiments, the polymeric mineral surface active agents may be polycarboxylates or polyphosphates or co-polymers of polymeric carboxylates such as Gantrez.

In some embodiments, the composition may comprise a fused silica and be essentially free of SLS. Essentially free means that there is less than about 0.01%, by weight of the composition. In some embodiments, the composition may further comprise a surfactant, other than SLS, selected from the group consisting of a nonionic surfactant, an anionic surfactant, a cationic surfactant, an amphoteric surfactant, a zwitterionic surfactant, and mixtures thereof. In some embodiments, the composition may further comprise a chelant. In some embodiments, the surfactant may be an amphoteric surfactant, such as betaine, for example. In some embodiments, the composition may have a PCR of at least about 80. In some embodiments, the surfactant may be at least about 50% available. In some embodiments, the composition has less than 3% of a surfactant, by weight of the composition. In some embodiments, the composition may further comprise a peroxide source and/or enzymes. Some embodiments may be a method of treating a dry mouth condition by administering to subject's oral cavity an oral composition comprising fused silica, wherein the composition is essentially free of sodium lauryl sulfate.

Method of Use

The present invention also relates to methods for cleaning and polishing teeth. The method of use herein comprises contacting a subject's dental enamel surfaces and oral mucosa with the oral compositions according to the present invention. The method of treatment may be by brushing with a dentifrice or rinsing with a dentifrice slurry or mouthrinse. Other methods include contacting the topical oral gel, mouthspray, toothpaste, dentifrice, tooth gel, tooth powders, tablets, subgingival gel, foam, mouse, chewing gum, lipstick, sponge, floss, petrolatum gel, or denture product or other form with the subject's teeth and oral mucosa. Depending on the embodiment, the oral composition may be used as frequently as a toothpaste, or may be used less often, for example, weekly, or used by a professional in the form of a prophy paste or other intensive treatment.

Additional Data

FIGS. 7-13 provide more detailed data on the material properties of fused silica, as well as its compatibility with other oral care composition components, and its cleaning ability.

FIGS. 7(a) and 7(b) are formula compositions and corresponding stannous, zinc, and fluoride compatibility data. FIG. 7(a) shows the oral care compositions, formula A comprising precipitated silicas, and formula B comprising fused silica. FIG. 7(b) shows the compatibility data for both formula A and B at 25° C. and at 40° C. after 2 weeks, 1 month, and 2 months, given as % compatibility. The data in FIG. 7 shows that the fused silica composition provides superior stability and compatibility with stannous, zinc, and fluoride.

It may be desired to have oral compositions with zinc salts wherein the composition has an availability of zinc of greater than about 82%, 85%, 87, or 90% after two weeks of storage at 25° C. It may be desired that the availability of 82%, 85%, 87% or 90% remain until before use by the consumer. Therefore, the availability may be measured before use. Before use can mean that the product has been made, packed, and distributed to a store or consumer but before the consumer has used the product. Storage conditions and temperatures during this time would vary.

It may be desired to have oral compositions with fluoride ions wherein the composition has a fluoride availability of greater than about 88%, 90%, 91%, 92%, 93%, or 94% after two weeks of storage at 25° C. It may also be desired that the fluoride availability remain at greater than about 88%, 90%, 91%, 92%, 93%, or 94% before use. For some formulations, fluoride availability may remain at greater than 95% before use.

It may be desired to have oral compositions with stannous salts wherein the composition has a compatibility or availability of stannous of greater than about 55%, 60%, 65%, 70%, 75%, 80%, 85%, or 90% after two weeks of storage at 25° C. Also, it may be desired that the stannous compatibility or availability remain at greater than about 55%, 60%, 65%, 70%, 75%, 80%, 85%, or 90% before use. It some compositions, the stannous availability or compatibility may be at least about 92%. For fused silica formulations with stannous, the stannous compatibility will typically be about 20% to about 50%, about 25% to about 45%, or about 30% to about 40% higher than formulations with comparable amounts of precipitated silica and stannous.

FIG. 8 shows the stannous compatibility as a function of load. The greater the amount of precipitated silica, the lower the amount of free or bioavailable stannous. The table demonstrates that the stannous loss to precipitated silica (Z-119) is 0.0081 g/g of Z-119 (or 80 ppm/1% Z-119 load). In contrast, the stannous loss to fused silica is 0.001 g/g of Tecosil 44CSS (or 10 ppm/1% Tecosil 44CSS load). In some embodiments, depending upon the surface area, the stannous loss to fused silica is from about 5 to about 50 ppm/1% load of fused silica, from about 7 to about 30 ppm/1% load of fused silica, from about 8 to about 20 ppm/1% load of fused silica, or from about 10 to about 15 ppm/1% load of fused silica.

FIGS. 9(a) and 9(b) are peroxide containing compositions and compatibility data. FIG. 9(a) shows peroxide-containing compositions with various precipitated and fused silicas. FIG. 9(b) shows the peroxide compatibility of the compositions, at 40° C., initially, after 6 days, and after 13 days. The data shows superior peroxide compatibility with the fused silicas over the precipitated silicas. In some embodiments, the peroxide compatibility is at least about 50%, at least about 60%, at least about 70%, at least about 80%, or at least about 85% after about 13 days at 40° C. Stated another way, in some embodiments, after about 13 days at 40° C., at least about 50%, 60%, 70%, or 85% of the peroxide or oxidizing agent may remain.

Method for sample preparation is as follows: Transfer 18 g of peroxide gel base in a plastic container; mix thoroughly 2 g of silica with spatula; measure pH of the mixture; divide the mixture into two equal parts and place one part at 25° C. and the other at 40° C.; place samples in stability chamber at 25° C. and 40° C. Sample analysis is as follows: Take an initial sample for peroxide analysis; take out samples from stability chambers at 5 and 12 days and allow to equilibrate for 1 day; remove 0.2 g of samples from each mixture and place remaining samples back in the stability chamber; perform peroxide analysis as follows: weigh 0.2000 g (+/−0.0200 g) of the peroxide gel into a 250 mL plastic beaker; add stir bar and 100 ml of 0.04N H2SO4, cover with parafilm, stir for at least 10 minutes; add 25 mL 10% KI solution and 3 drops of NH4-Molybdate and stir additional 3-20 minutes; analyze via autotitration with 0.1N Na-Thiosulfate. Compatibility is defined as the peroxide percent after 13 days at 40° C. divided by the initial peroxide percent, then multiplied by 100. It is known to those of ordinary skill in the art that a product placed at 40° C. represents an extended shelf life. That is, for example, one month at 40° C. would roughly approximate eight months at room temperature.

FIG. 10(a) shows formulas A-E that are oral care compositions comprising fused silica and peroxide. FIG. 10(b) shows the change in brightness (Δ L) of bovine enamel specimens after a given number of brush strokes for two of the compositions in FIG. 10(a) that have fused silica and peroxide, in comparison to a formula with fused silica but not peroxide (formula F), and a formula with neither fused silica nor peroxide (Crest Cavity Protection Toothpaste). The data demonstrates that the combination of fused silica and peroxide delivers superior cleaning and whitening. In some embodiments, the delta L may be greater than about 4.5 at 50 strokes, greater than about 6.0 at 100 strokes, greater than about 9.0 at 200 strokes, or greater than about 15.0 at 400 strokes. In some embodiments, the delta L may be from about 50% to about 100% greater than Crest Cavity Protection Toothpaste. The method is as follows: Substrates of bovine enamel are mounted and stained per conventional PCR protocol described by G. K. Stookey, et al., *J. Dental Res.*, 61, 1236-9, 1982. Groups of 6 chips are divided for each treatment leg, with each group having approximately the same baseline L value. 1:3 slurries of treatment paste are made and stained bovine enamel substrates are brushed for 50, 100, 200, and 400 strokes with a calibrated force of 150 grams exerted during brushing. After brushing with each number of strokes the substrates are imaged and analyzed for L values. Change in L values are calculated as follows: $\Delta L = L_{post-brush} - L_{pre-brush}$ and compared statistically using LSD FIG. 11(a) shows dentifrice composition formulas comprising precipitated or fused silicas, and FIG. 11(b) shows corresponding consumer perception data. The consumer perception test was performed among nine subjects who brushed with each product twice and provided feed back via written questionnaire to questions related to flavor display and mouth feel. The subjects were asked to provide feedback about their experience during use, immediately after use and 15 minutes after using the product. As shown in FIG. 11(*b*), in general, the compositions comprising fused silica offer superior flavor intensity, refreshment, slick tooth feel, and clean mouth, when compared to precipitated silica used in formula A.

Figures 12, 12A, 12B:
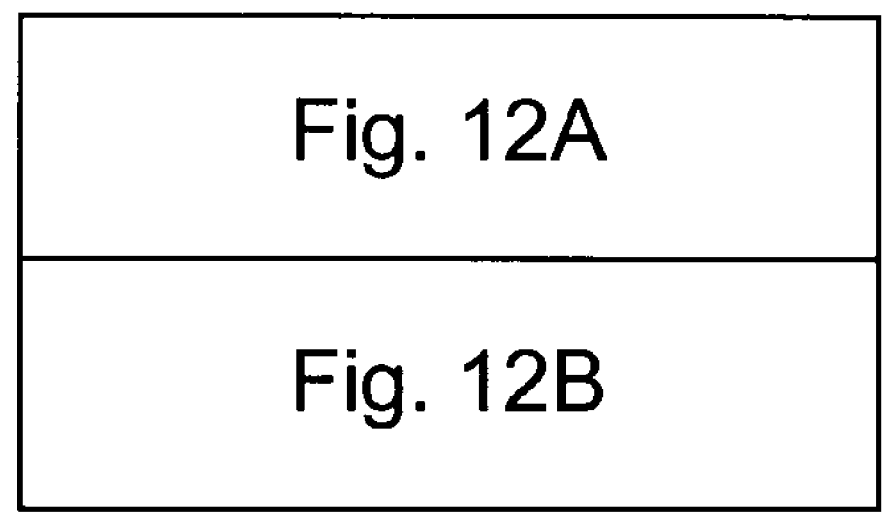

FIG. 12 shows additional example formulas of oral care compositions comprising fused silica. The formulas include compositions comprising a gel network, combinations of fused silica with precipitated silica and with calcium carbonate, compositions that are free of SLS, and compositions that may be used as a prophy paste or used on a non-daily basis.

FIG. 13(*a*) shows sodium fluoride based compositions in which formulas A and B comprise precipitated silicas with traditional thickeners, formulas C and D comprise fused silica with traditional thickeners, and formulas E and F comprise fused silica with a gel network. FIG. 13(*b*) is a table of RDA and PCR values for the sodium fluoride-based compositions of FIG. 13(*a*), showing that use of fused silica improves the cleaning ability of a composition, and that use of a gel network improves the cleaning ability of the composition even more, all while still having acceptable abrasivity. FIG. 13(*c*) shows stannous fluoride based compositions in similar embodiments to FIG. 13(*a*). FIG. 13(*d*) shows the corresponding RDA values for the FIG. 13(*c*) compositions, indicating that the use of stannous may decrease abrasion, showing the potential strengthening of teeth by stannous formulas.

NON-LIMITING EXAMPLES

The dentifrice compositions illustrated in the following examples illustrate specific embodiments of the dentifrice compositions of the present invention, but are not intended to be limiting thereof. Other modifications can be undertaken by the skilled artisan without departing from the spirit and scope of this invention.

Example I

A-D are typical oral compositions comprising fused silica. Formula B shows a combination of fused and precipitated silicas, and formula D a combination of fused silica and calcium carbonate:

| Ingredient | A | B | C | D |
|---|---|---|---|---|
| Sodium Fluoride | 0.24 | 0.24 | — | — |
| Sodium Monofluorophosphate | — | — | 1.13 | 1.13 |
| Sorbitol | 59.58 | 59.58 | 59.58 | 24.00 |
| Glycerin | — | — | — | — |
| Silica (Zeodent 119) | — | 15.00 | — | — |
| Silica (Zeodent 109) | — | — | — | — |
| Fused Silica (Teco-Sil 44CSS) | 15.00 | 5.00 | 15.00 | 10.00 |
| Calcium carbonate | — | — | — | 30.00 |
| Sodium Phosphate Tribasic | 1.10 | 1.10 | 1.10 | 0.40 |
| Flavor | 0.81 | 0.81 | 0.81 | 1.00 |
| Carboxymethylcellulose Sodium | 0.75 | 0.75 | 0.75 | 1.30 |
| Carrageenan | — | — | — | — |
| Xanthan Gum | — | — | — | — |
| Titanium Dioxide | 0.53 | 0.53 | 0.53 | — |
| Sodium Phosphate, Monobasic | 0.42 | 0.42 | 0.42 | 0.10 |
| Carbomer 956 | 0.30 | 0.30 | 0.30 | — |
| Saccharin Sodium | 0.13 | 0.13 | 0.13 | 0.20 |
| FD&C Dyes | 0.05 | 0.05 | 0.05 | — |
| Sodium Lauryl Sulfate | 4.00 | 4.00 | 4.00 | 7.00 |
| Water | QS | QS | QS | QS |
| | 100.00 | 100.00 | 100.00 | 100.00 |

Example II

A-F are typical oral compositions comprising fused silica with cationic antimicrobials:

| Ingredient | A | B | C | D | E | F |
|---|---|---|---|---|---|---|
| Sodium Fluoride | — | — | — | — | — | 0.24 |
| Stannous Fluoride | 0.45 | 0.45 | 0.45 | 0.45 | 0.45 | — |
| Stannous Chloride | 1.16 | 1.16 | 1.16 | — | — | — |
| Sodium gluconate | 1.06 | 1.06 | 1.06 | 1.06 | 1.06 | — |
| Zinc Citrate | 0.53 | 0.53 | 0.53 | — | — | — |
| Zinc Lactate | — | — | — | 2.50 | 2.50 | 2.00 |
| Cetyl pyrinidium chloride | — | — | — | — | — | 0.25 |
| Sodium hexametaphosphate | — | — | — | 13.00 | 13.00 | — |
| PEG 300 | — | — | — | 7.00 | 7.00 | 7.00 |
| Sodium triployphsophate | — | — | 5.00 | — | — | 5.00 |
| Phytic acid | 0.80 | 0.80 | — | — | — | — |
| Sorbitol | 38.07 | 38.07 | 38.07 | — | — | 50.00 |
| Glycerin | — | — | — | 55.33 | 55.33 | 8.00 |
| Silica (Zeodent 119) | — | — | — | — | 5.00 | — |
| Silica (Zeodent 109) | — | 7.50 | 5.00 | — | — | — |
| Fused Silica (Teco-Sil 44CSS) | 15.00 | 7.50 | 10.00 | 15.00 | 10.00 | 15.00 |
| Flavor | 1.20 | 1.20 | 1.20 | 1.00 | 1.00 | 1.00 |
| Carboxymethylcellulose Sodium | 1.30 | 1.30 | 1.30 | — | — | 1.30 |
| Carrageenan | — | 0.70 | 0.70 | 0.60 | 0.60 | — |
| Xanthan Gum | — | — | — | 0.25 | 0.25 | 0.25 |
| Titanium Dioxide | 0.50 | 0.50 | 0.50 | — | — | — |
| Saccharin Sodium | 0.25 | 0.25 | 0.25 | 0.25 | 0.25 | 0.25 |
| FD&C Dyes | — | — | — | 0.05 | 0.05 | 0.05 |
| Sodium Lauryl Sulfate | 7.50 | 7.50 | 7.50 | 3.50 | 3.50 | 3.50 |
| Water | QS | QS | QS | QS | QS | QS |
| | 100.00 | 100.00 | 100.00 | 100.00 | 100.00 | 100.00 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it will be obvious to those skilled in the art that various changes and modifications may be made without departing from the spirit and scope of the invention. It is therefore intended to cover in the appended claims all such changes and modifications that are within the scope of the invention.

We claim:

1. An oral care composition comprising:
   a) from about 20% to about 50%, by weight of the composition, of fused silica, wherein said fused silica has a particle size with a D90 of less than about 50 microns and wherein at least 25% of the fused silica particles are spherical;
   b) from about 0.0025% to about 5.0% by weight of the composition of stannous fluoride;
   c) from about 0.001% to about 20% by weight of the composition of an antimicrobial agent; and
   d) from about 0.1% to about 20%, by weight of the composition, of a chelating agent.

2. The composition of claim 1, wherein the composition has an RDA of less than about 150.

3. The composition of claim 1, wherein the composition has an RDA of less than about 120.

4. The composition of claim 1, wherein the ratio of PCR to RDA is at least about 0.7.

5. The composition of claim 1, wherein the ratio of PCR to RDA is at least about 0.9.

6. The composition of claim 1, wherein the ratio of PCR to RDA is at least about 1.0.

7. The composition of claim 1, wherein the composition has an RDA of less than about 170.

8. The composition of claim 1, further comprising a fused silica wherein at least 25% of the fused silica particles are angular.

9. The composition of claim 8, wherein the amount of the angular fused silica is from about 1% to about 10%, by weight of the composition.

10. The composition of claim 1, wherein the median particle size of the fused silica is from about 3.0 microns to about 15.0 microns.

* * * * *